United States Patent
Appel et al.

(10) Patent No.: US 11,045,429 B2
(45) Date of Patent: Jun. 29, 2021

(54) SHEAR-THINNING SELF-HEALING NETWORKS

(71) Applicant: Massachusetts Institute of Technology, Cambridge, MA (US)

(72) Inventors: Eric A. Appel, Cambridge, MA (US); Mark W. Tibbitt, Aarau (CH); Robert S. Langer, Newton, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 15/412,935

(22) Filed: Jan. 23, 2017

(65) Prior Publication Data
US 2017/0319506 A1 Nov. 9, 2017

Related U.S. Application Data

(63) Continuation of application No. PCT/US2015/052036, filed on Sep. 24, 2015.

(60) Provisional application No. 62/054,522, filed on Sep. 24, 2014, provisional application No. 62/187,940, filed on Jul. 2, 2015.

(51) Int. Cl.
| | | |
|---|---|---|
| *A61K 9/51* | (2006.01) | |
| *A61K 9/06* | (2006.01) | |
| *A61K 47/36* | (2006.01) | |
| *A61K 47/38* | (2006.01) | |
| *A61K 47/30* | (2006.01) | |
| *A61K 47/34* | (2017.01) | |

(52) U.S. Cl.
CPC .............. *A61K 9/5161* (2013.01); *A61K 9/06* (2013.01); *A61K 9/5146* (2013.01); *A61K 9/5153* (2013.01); *A61K 47/30* (2013.01); *A61K 47/34* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | | | |
|---|---|---|---|---|
| 2007/0129282 A1* | 6/2007 | Ahlem | ................... | A61K 31/56 514/63 |
| 2010/0285113 A1* | 11/2010 | Shoichet | .............. | A61K 9/0024 424/450 |
| 2012/0213708 A1* | 8/2012 | Anderson | ............ | A61K 9/0019 424/9.2 |
| 2013/0189230 A1* | 7/2013 | Shoichet | .............. | A61K 9/0024 424/93.7 |
| 2015/0202299 A1* | 7/2015 | Burdick | ................ | A61L 31/042 424/85.2 |
| 2015/0250891 A1* | 9/2015 | Venkatraman | ....... | A61K 9/0014 424/450 |

FOREIGN PATENT DOCUMENTS

| | | |
|---|---|---|
| WO | WO-2003084481 A2 | 10/2003 |
| WO | WO-2005110377 A1 | 11/2005 |
| WO | WO-2013076305 A1 | 5/2013 |
| WO | WO-2013124654 A1 | 8/2013 |
| WO | WO-2014116187 A1 | 7/2014 |
| WO | WO-2015172073 A1 | 11/2015 |

OTHER PUBLICATIONS

Xiao e al. "Recent advances in PEG-PLA block copolymer nanoparticles" Nov. 2010.*
Riley et al. "Core-Shell Structure of PLA-PEG Nanoparticles used for Drug Delivery" Aug. 2003.*
Khoee et al. "Effects of hydrophobic drug-polyesteric core interactions on drug loading and release properties of polyethylene glycol)-polyester-poly(ethylene glycol) triblock core-shell nanoparticles" May 2007.*
Bao et al. "Interactions between Ionic Surfactants and Polysaccharides in Aqueous solutions" Nov. 2008.*
Akay et al. Self-healing hydrogels formed in cationic surfactant solutions. 2013.*
Patterson et al., "In Situ Characterization of the Degradation of PLGA Microspheres in Hyaluronic Acid Hydrogels by Optical Coherence Tomography," IEEE Transactions on Medical Imaging, vol. 28 (2009): 74-81.
Wang et al., "PLGA-chitosan/PLGA-alginate nanoparticle blends as biodegradable colloidal gels for seeding human umbilical cord mesenchymal stem cells," *Journal of Biomedical Materials Reasearch*. Part A, vol. 96A (2011):520-527.
International Search Report and Written Report in International Application No. PCT/US2015/052036, dated Dec. 23, 2015, 14 pages.

\* cited by examiner

*Primary Examiner* — Danah Al-Awadi
(74) *Attorney, Agent, or Firm* — Pabst Patent Group LLP

(57) ABSTRACT

Network materials which exhibit both shear thinning and self-healing properties are disclosed. The networks contain particles and gel-forming compounds. The networks are useful for a variety of biomedical uses, including drug delivery.

36 Claims, 14 Drawing Sheets

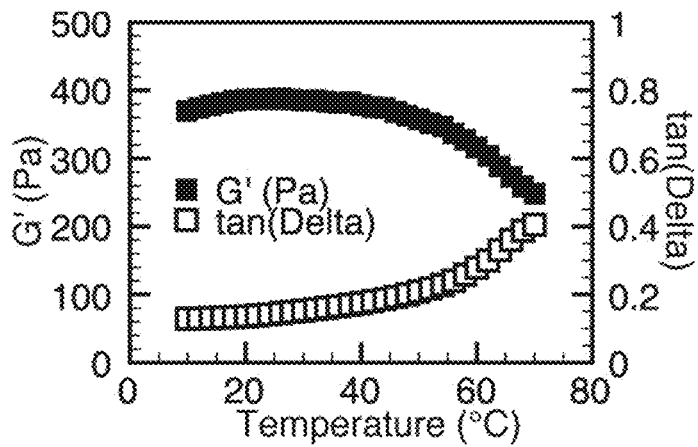
Fig. 2m
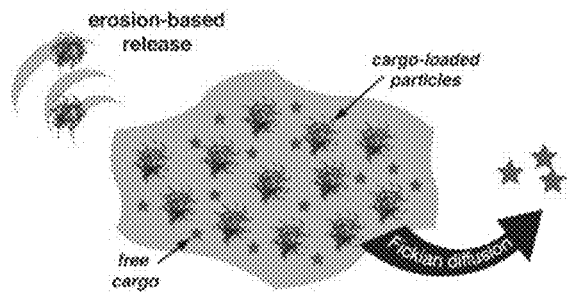
Fig. 3
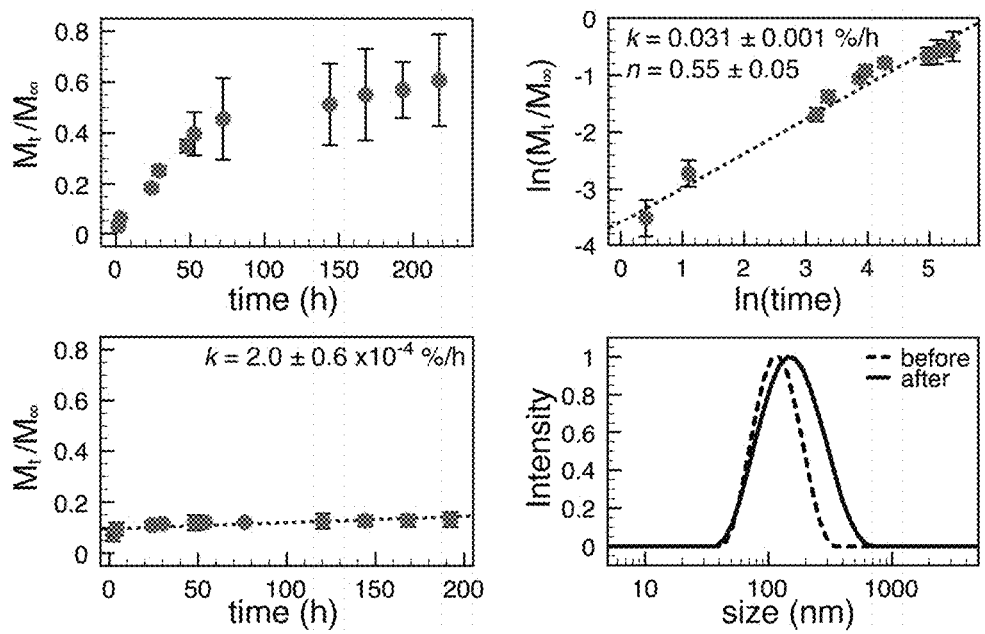
Fig. 4a-d

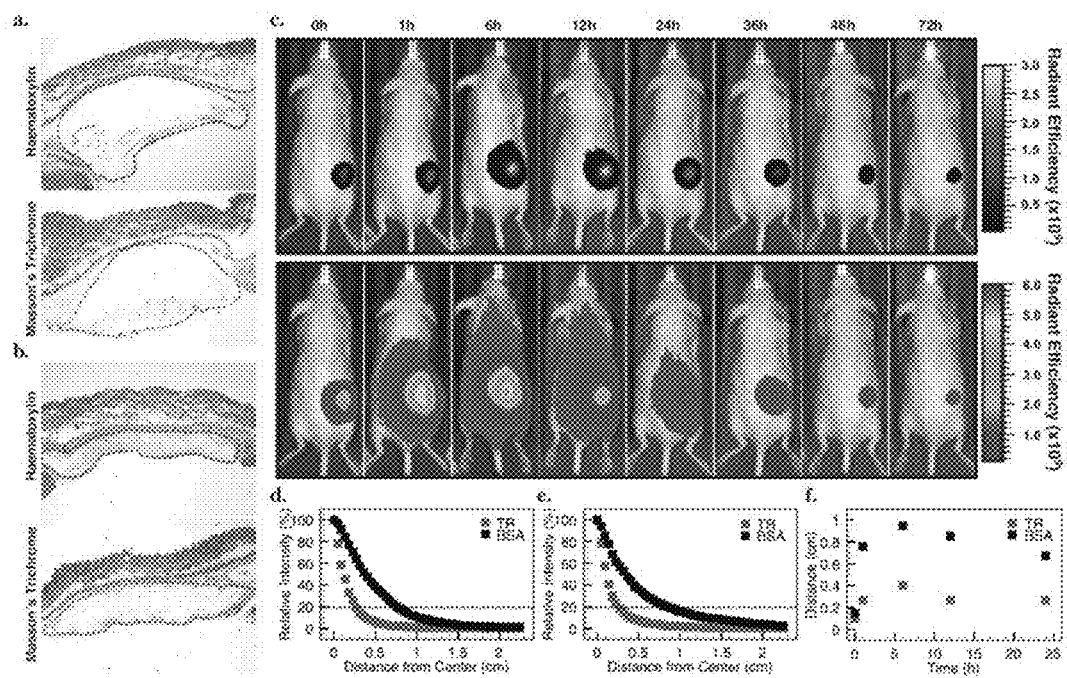
Fig. 5a-f

Long-term Delivery of Biologics from PNP Hydrogels

BSA release from HPMC-C12 (0.75%), MC (0.25%), and PEG-PLA NPs (10%) with a diffusional release coefficient of $k = 5.3\%/day$.

IgG release from HPMC-C12 (0.9%), MC (0.1%), and PEG-PLA NPs (10%) with a diffusional release coefficient of $k = 8.4\%/day$

SHEAR-THINNING SELF-HEALING NETWORKS

CROSS-REFERENCE TO RELATED APPLICATIONS

This application is a bypass continuation application of International Application No. PCT/US2015/052036, filed on Sep. 24, 2015 and entitled "Shear-Thinning Self-Healing Networks," which in turn claims a priority benefit to U.S. Provisional Application No. 62/187,940, filed Jul. 2, 2015 and U.S. Provisional Patent Application No. 62/054,522, filed Sep. 24, 2014. Each of the aforementioned applications is incorporated herein by reference.

STATEMENT REGARDING FEDERALLY SPONSORED RESEARCH

This invention was made with government support under Grant RO 1 DE0156516 to Robert S. Langer, awarded by the National Institutes of Health. The government has certain rights in the invention.

FIELD

This application is directed to shear-thinning, self-healing network materials. More particularly the shear-thinning, self-healing network materials are polymer nanoparticle networks. These materials are useful for a range of industrial and biomedical applications.

BACKGROUND

Solvated gels comprise an important class of materials well-suited for a range of industrial and biomedical applications on account of their lubricity and similarity to soft biological tissue and highly tunable mechanical properties. Many gel systems utilize covalent cross linking approaches in order to form robust, tough and materials. However, such systems can be limited by the irreversibility of the covalent crosslinks. Recently, rationally designed non-covalent interactions that provide reversible control over the self-assembly process, have yielded new types of moldable gels, which must exhibit viscous flow under shear stress (shear-thinning) and rapid recovery when the applied stress is relaxed (self-healing). Shear-thinning and self-healing materials exhibit many unique and useful properties, including externally tunable strength, moldability, low-energy synthesis/processing, and self-healing.

Several classes of these materials have been developed and evaluated in various applications and exploit many different types of interactions for non-covalent crosslinking including host-guest interactions, ionic interactions, metal-ligand coordination, rationally-designed biopolymer self-assembly, as well as natural biopolymer crosslinking. Self-assembly via non-covalent crosslinking provides a route to fabricate moldable and injectable gels with shear-thinning and self-healing properties arising from strong, yet transient and reversible cross-links. Natural host-guest or receptor ligand pairs, such as (strept)avidin with biotin, exhibiting extremely high binding affinity, have been described previously. However, their use has been hampered by difficulties in chemical modification and synthetic scalability. Leucine zippers, a subcategory of coiled-coil domains found widely in nature that assemble into clusters, have been utilized as junction points for hydrogel formation. The coiled-coil motif has been exploited in both telechelic and graft polymers to produce a wide array of protein hydrogels. Injectable shear-thinning hydrogels utilizing self-assembling "dock-and-lock" protein structures prepared with genetic engineering techniques have also been explored. Additionally, supramolecular hydrogels exhibiting rapid recovery of mechanical properties have been prepared leveraging the dynamics of host-guest systems of macrocyclic oligomers, cyclodextrins (CD) and cucurbit[n]urils (CB[n]) that form inclusion complexes with a wide variety of guest molecules. Clay-based hydrogels have been modified with polymeric binders, which facilitate the incorporation of active agents. However, because the clay forms a gel in the absence of any other components, the system is not easily adaptable for many biomedical applications as it is not readily injectable.

In each of these examples, self-assembly was used to fabricate functional material via non-covalent, intermolecular interactions with dynamic and reversible macroscopic behavior. However, the shear-thinning and self-healing hydrogels presented to date are limited by poor mechanics and slow self-healing, and often require challenging and costly synthesis of macromolecular components. Furthermore, in all of these systems developed to date, specific interactions between polymers and nanoparticles have not been leveraged for gel formation. In examples comprising nanoparticles, the nanoparticles were employed either as additives to existing gels to increase their mechanical properties or constituted a gel alone prior to the addition of other components.

SUMMARY

There exists a need for shear-thinning, self-healing gels with improved mechanics and faster self-healing that can be synthesized in a straight-forward, cost-effective manner.

Therefore, it is an object of the invention to provide shear-thinning, self-healing gels with improved mechanics, faster self-healing, and facile preparation.

It is an object of the invention to provide a platform in which the properties of the shear-thinning, self-healing gels can be modulated by appropriate selection of the constituents and constituent chemical functionality in the gel materials.

It is a further object of the invention to provide a facile method for the preparation shear-thinning, self-healing gels that do not require costly or impractical starting materials and/or synthetic methods.

It is also an object of the invention to provide shear-thinning, self-healing gels which can be incorporated with a variety of bioactive agents. It is a further object of the invention to provide a gel allowing for the controlled release of bioactive agents.

Disclosed herein are shear-thinning, self-healing networks formed from appropriately paired nanoparticles and polymers. These polymer-nanoparticle (PNP) gels form rapidly upon mixing of solutions of said appropriately paired polymers and nanoparticles. The polymers selectively adsorb to the nanoparticles to form non-covalent cross-links, yielding gel formation. Owing to the dynamic and transient nature of the cross-links, these gels exhibit dramatic shear-thinning and rapid self-healing. The polymers and nanoparticles envisioned for these shear-thinning, self-healing PNP gels each independently do not form a gel alone or are not used at a concentration where the polymer alone or nanoparticle alone form a gel, and that only when the nanoparticle and polymer are combined does gel formation occur.

Provided herein are polymer nanoparticle (PNP) gels which comprise one or more gel-forming polymer and a particle, wherein the loss modulus (G") for a solution of the one or more gel-forming polymer and the loss modulus (G") of a solution of the particle are each greater than the respective storage moduli (G') at a frequency of 10 rad/s as measured by oscillatory shear rheometry in the linear viscoelastic regime; and wherein the particle and the one or more gel-forming polymer form a PNP gel when combined. The storage modulus (G') for the resulting PNP gel is greater than the loss modulus (G") at a frequency of 10 rad/s as measured by oscillatory shear rheometry in the linear viscoelastic regime when combined In some embodiments of the PNP gels, the dynamic shear viscosity of the PNP gel at a shear rate within the range between $0.1\ s^{-1}$ to $100\ s^{-1}$ is greater than the sum of the dynamic shear viscosity of the nanoparticle solution and the gel-forming polymer solution at said shear rate within the range between $0.1\ s^{-1}$ to $100\ s^{-1}$.

In some embodiments of the PNP gels, the dynamic shear viscosity of the PNP gel at a shear rate within the range between $0.1\ s^{-1}$ to $100\ s^{-1}$ is a multiplicative factor of 2 to 100,000 times greater than the sum of the dynamic shear viscosity of the nanoparticle solution and the gel-forming polymer solution at said shear rate within the range between $0.1\ s^{-1}$ to $100\ s^{-1}$. In other embodiments, the multiplicative factor is between 2 to 1,000 times greater. In still other embodiments, the multiplicative factor is between 2 to 100 times greater. In further embodiments, the multiplicative factor is between 2 to 10 times greater.

BRIEF DESCRIPTION OF THE DRAWINGS

FIGS. 2a-d are graphs showing the oscillatory rheological properties of hydrogels from (a) $HPMC_{12}$ 1% with PSNPs 10% of various sizes; (b) $HPMC_{12}$ with PSNP (50 nm) at various loadings, and (c) HPMC-X bearing various functionality (0.5 mmol/g) at 1% with PSNPs (50 nm) at 10% (all values taken at w=10 rad/s and γ=2%). FIG. 2d depicts the oscillatory rheological properties of hydrogels from $HPMC-C_{12}$ (1%) with PSNPs of two different sizes: 50 nm (5 wt %) and 500 nm (1, 3 and 5 wt %) (all values taken at w=10 rad/s and γ=2%). FIGS. 2e and 2f are graphs showing the strain-dependent (w=10 rad/s, FIG. 2e) and frequency-dependent (γ=2%, FIG. 2f) oscillatory shear rheology of $HPMC-C_{12}$ 1%/PSNP 10% hydrogels. FIG. 2g is a graph showing the step-strain measurements of $HPMC-C_{12}$ 1%/PSNP 10% hydrogels over three cycles with overlaid zoom of the recovery material properties after each cycle (FIG. 2h). FIG. 2i is a graph showing the oscillatory rheological properties of hydrogels from HPMC-X bearing various functionality (0.5 mmol/g) at 1% with PEG-PLA NPs at 10%. FIG. 2j is a graph showing the frequency-dependent (γ=2%) oscillatory shear rheology of $HPMC-C_{12}$ 1%/PEG-b-PLA NPs 10% hydrogels. FIG. 2k is a graph showing the step-strain measurements of $HPMC-C_{12}$ 1%/PEG-b-PLA NP 10% hydrogels over three cycles with overlaid zoom of the recovery material properties after each cycle (FIG. 2l). FIG. 2m is graph showing the temperature sweep (10-70° C.) of rheological properties of $HPMC-C_{12}$ 1%/PSNP 10% hydrogels.

FIG. 3 is a schematic representation of two stage release of therapeutic cargo allowing for facile tuning of drug release profile.

FIG. 4a is a graph showing the drug release profile of Bovine Serum Albumin (BSA; hydrophilic) from hydrogels.

FIG. 4b is a graph showing the fitting of the release data for BSA, demonstrating release by Fickian diffusion.

FIG. 4c is a graph showing the drug release profile of Oil Red (OR; hydrophobic) from hydrogels prepared with OR-loaded PEG-b-PLA NPs. FIG. 4d depicts a dynamic light scattering (DLS) characterization of PEG-b-PLA NPs immediately after preparation, and subsequent to erosion in supernatant.

FIG. 5a shows the histological analysis of Masson's trichrome and haematoxylin stained samples taken after 3 days.

FIG. 5b shows the histological analysis of Masson's trichrome and haematoxylin stained samples taken after 7 days. The interface between biological tissue and PNP gels are denoted with a dotted line.

FIG. 5c are intravital fluorescence images of the release of TR (top) and BSA-AF (bottom) from a single material. Plots of relative intensity of model therapeutic fluorescence vs. distance from the center of the hydrogel implant at 1 h (FIGS. 5d) and 12 h (FIG. 5e, n=5).

FIG. 5f is a graph showing the radius of release at 20% relative fluorescence intensity over time.

FIG. 12b is a graph of IgG release from HPMC-C12 (0.9%), MC (0.1%), and PEG-PLA NPs (10%) with a diffusional release coefficient of k=8.4%/day.

DETAILED DESCRIPTION

I. Definitions

Figure 1:
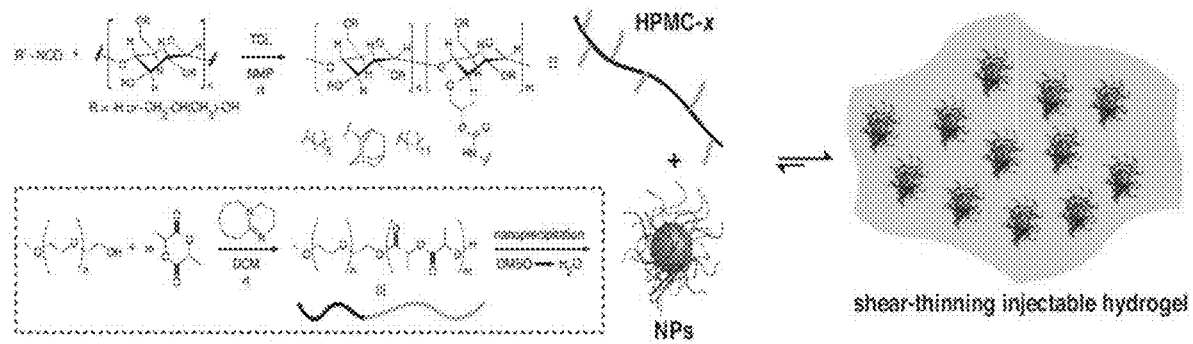
FIG. 1 is a schematic representation of the preparation of dynamically crosslinked and shear-thinning injectable hydrogels utilizing non-covalent interactions between core-shell nanoparticles (NPs) and hydrophobically-modified hydroxypropylmethylcellulose (HPMC-x). The hydrophobic core of the NPs can be composed of either poly(styrene) (PS; non-degradable) or poly(lactic acid) (PLA; biodegradable).

As used herein, the term "network" refers to a percolated, three dimensional substance that is crosslinked via interactions between chemical entities. In some embodiments, these entities are particles and a continuous phase. In some embodiments, the particles are nanoparticles. In some embodiments, the continuous phase is made of polymeric compounds.

As used herein, the term "continuous phase" refers to the compound or compounds with which the particles interact to form a network. The continuous phase may be made of polymeric compounds, non-polymeric compounds, or mixtures thereof, so long as the continuous phase exclusively forms a network when mixed with said particles.

The term "gel," as used herein, refers to a cross-linked (covalently, non-covalently, or both) network having a volume fraction that is a solvent. When the solvent is water or another aqueous solution, the network may be designated a "hydrogel." When the solvent is not water-based, the network may be designated an "organogel." Unless otherwise modified, the term "gel" embraces both hydrogels and organogels.

As used herein, the term "gel-forming" refers to the ability of a compound or polymer to form a gel upon mixing with an appropriately paired particle. Unless otherwise modified, the term "gel" embraces both hydrogels and organogels.

"Shear-thinning," as used herein, refers to the effect where a gel's viscosity—the measure of a fluid's resistance to flow—decreases with an increasing rate of shearing or increased shear stress. The stress is typically applied via physical force and/or pressure.

"Self-healing," as used herein, refers to a process in which a gel having reduced resistance to flow when subject to external stress, regains some, or all, of its rigidity and strength after the external stress is removed.

"Bioactive agent" and "active agent" are used interchangeably and include without limitation physiologically or pharmacologically active substances that act locally or systemically in the body, such as therapeutic, prophylactic, and/or diagnostic agents. A biologically active agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment. Examples can include, but are not limited to, small-molecule drugs, peptides, proteins, antibodies, sugars, polysaccharides, nucleotides, oligonucleotides, aptamers, siRNA, nucleic acids, and combinations thereof. "Bioactive agent" includes a single such agent and is also intended to include a plurality of bioactive agents including, for example, combinations of two or more bioactive agents.

As used herein, the term "pharmaceutically acceptable salt" refers to a salt prepared from pharmaceutically acceptable non-toxic acids and bases, including inorganic acids and bases, and organic acids and bases. Suitable non-toxic acids include inorganic and organic acids such as acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like. Suitable positively charged counterions include sodium, potassium, lithium, calcium and magnesium.

"Small molecule," as used herein, refers to molecules with a molecular weight of less than about 2000 Daltons, about 1500 Daltons, about 1200 Daltons, about 1000 Daltons, about 750 Daltons, or about 500 Daltons.

"Copolymer" is used herein to refer to a polymeric material that is comprised of two or more different monomers. The copolymer can be of any form, such as random, block, graft, etc. The copolymers can have any end-group.

The term "biocompatible", as used herein, refers to materials that are, along with any metabolites or degradation products thereof, generally non-toxic to the recipient, and do not cause any significant adverse effects to the recipient, at concentrations resulting from the degradation of the administered materials. Generally speaking, biocompatible materials are materials which do not elicit a significant inflammatory or immune response when administered to a patient.

"Biodegradable" refers to a material that will degrade or erode under physiologic conditions to smaller units or chemical species that are capable of being metabolized, eliminated, or excreted by the subject.

"Molecular weight," as used herein with reference to polymeric materials, unless otherwise specified, refers to the relative average chain length of the bulk polymer. In practice, molecular weight can be estimated or characterized in various ways including gel permeation chromatography (GPC) or capillary viscometry. GPC molecular weights are reported as the number-average molecular weight (Mn) as opposed to the weight-average molecular weight (Mw). Capillary viscometry provides estimates of molecular weight (Mv) as the inherent viscosity determined from a dilute polymer solution using a particular set of concentration, temperature, and solvent conditions.

"Mean particle size" refers to the statistical mean particle size (diameter) of the particles in the composition. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution", are used interchangeably herein and describe a population of nanoparticles or microparticles where all of the particles are the same or nearly the same size. As used herein, a monodisperse distribution refers to particle distributions in which 90% of the distribution lies within 15% of the median particle size, more preferably within 10% of the median particle size, most preferably within 5% of the median particle size.

"Controlled release" or "modified release," as used herein, refers to a release profile in which the drug release characteristics of time course and/or location are chosen to accomplish therapeutic or convenience objectives not offered by conventional dosage forms such as solutions, suspensions, or promptly dissolving dosage forms. Delayed release, extended release, and pulsatile release and their combinations are examples of modified release.

"Delayed release" as used herein refers to release of a drug (or drugs) at a time other than promptly after administration.

"Extended release" as used herein refers to release of a drug (or drugs) that allows at least a twofold reduction in dosing frequency as compared to the drug presented as a conventional dosage form (e.g. as a solution or prompt drug-releasing, conventional solid dosage form).

"Pulsatile release" as used herein refers to release of a drug (or drugs) that mimics a multiple dosing profile without repeated dosing and allows at least a twofold reduction in dosing frequency as compared to the drug presented as a conventional dosage form (e.g. as a solution or prompt drug-releasing, conventional solid dosage form). A pulsatile release profile is characterized by a time period of no release (lag time) or reduced release followed by rapid drug release.

The term "microparticle" is used herein to refer to structures or particles having sizes from about 1 micron to about 1000 microns and includes microcapsules, microspheres, nanoparticles, nanocapsules, nanospheres, as well as particles, in general that are less than about 1000 microns.

"Nanoparticle," as used herein, generally refers to a particle having a diameter from about 1 nm up to, but not including, about 1 micron, or from about 25 nm to about 1 micron. In one embodiment, the particles have a mean size of less than about 90 nm. In another embodiment less than about 80 nm, In another embodiment from about 50 nm to about 80 nm. In other embodiments, the particles have a mean size from about 30 nm to 50 nm. The particles can have any shape. Nanoparticles having a spherical shape are generally referred to as "nanospheres."

"Core-shell particles" and "core-corona particles," as used herein, refer to particles containing a core containing or formed from one material, and a shell or corona containing or formed from a second different material.

Unless otherwise specified, the term "nanoparticle" includes both homogenous nanoparticles and core-shell/core-corona particles.

The term "homogenous nanoparticle," as used herein, is to differentiate core-shell/core-corona particles from non-core-shell particles. The modifying adjective "homogenous" is not to be taken to mean that the particle is uniformly made from a single component, but rather that the particle does not contain two disparate phases as found in a core-shell/core-corona particle.

The particles may be spherical or non-spherical in shape. A microcapsule or nanocapsule is generally a particle that has a heterogeneous structure whereby the particle is covered by a substance or coating of some type, often a polymer or polymeric material or a wall-forming material. When the particle contains an agent (such as a bioactive agent or other excipient or additive), the agent is generally heterogeneously distributed in the particle and is typically centrally located within the membrane or coating. A microcapsule can also include microbubbles (hollow particle), porous microbubbles, porous microcapsules, and particles in general that comprise a central core surrounded by a unique outer membrane. In contrast, a microsphere or nanosphere has a more homogeneous structure whereby any incorporated agents are more or less distributed throughout the matrix of the particle where the remainder of the matrix is comprised of a polymer or polymeric material or matrix-forming material. A microsphere or nanosphere can include porous microspheres or nanospheres.

"Needle" is used herein to refer to devices that can be used to administer, deliver, inject, or otherwise introduce a gel formulation to a subject for any purpose(s) including medical, clinical, surgical, therapeutic, pharmaceutical, pharmacological, diagnostic, cosmetic, and prophylactic purposes. Thus, as defined herein, needle includes needle, all needle-like devices, and all other annular gel introduction devices, such as tubing, etc. Specific examples include needles, hypodermic needles, surgical needles, infusion needles, catheters, trocars, cannulas, tubes, and tubing used for clinical, surgical, medical, procedural, or medical purposes.

"Injected", "injection", or "injectability" as used herein is intended to include any administration of the gel, such as by injection, infusion, or any other delivery through any annular delivery device to the subject. Injection includes delivery through a tube.

The term "gauge" refers to the needle size in terms of a gauge scale. A lower gauge number indicates a larger inner diameter. Gauge size versus the needle inner diameter is typically standardized but some variations can occur. The outer and inner diameter of the needle, expressed in inches and millimeters, for gauge sizes described herein are from the 2007 Product Guide for BD Precision Glide™ hypodermic needle tubing specifications.

II. Shear Thinning, Self-Healing Compositions

Moldable PNP gel networks that flow upon applied stress and rapidly self-heal are described herein. Self-assembly of the PNP gel networks occurs when polymers are linked together by selective adsorption onto nanoparticles through multivalent transient interactions. These transient and reversible interactions between polymers and nanoparticles enable flow under applied shear stress, followed by rapid self-healing when the stress is relaxed. Such networks can be implanted into animals, including humans, in a minimally invasive manner and conform to the local geometry upon application.

The PNP gels of the present invention form rapidly upon mixing of solutions of appropriately paired polymers and nanoparticles, such that the polymers selectively adsorb to the nanoparticles, and exhibit dramatic shear-thinning and rapid self-healing. Any polymer having the ability to form PNP gels with nanoparticles is useful in the present invention. For example polymers that comprise functionality capable of interacting with the appropriate nanoparticle are useful.

Efficient crosslinking between polymers and nanoparticles in PNP gel networks is governed by three important parameters:

i. affinity between nanoparticles and polymers where the free energy gain is greater than thermal energy ($\varepsilon > k_B T$), ii. the number of crosslinking interactions (n), and iii. nanoparticle size relative to the persistence length of the polymers ($D_H \leq l_P$).

The strength of the materials (G), therefore, can be related to the number of polymer-nanoparticle interactions per unit volume (n) and the energy associated with each interaction ($\alpha k_B T$) using theoretical tools analogous to those developed for covalent hydrogels: $G \approx n\alpha k_B T$.

Moldable hydrogels must exhibit viscous flow under shear stress (shear-thinning) and rapid recovery when the applied stress is relaxed (self-healing). In addition, it is extremely beneficial if the high shear viscosity is low (i.e., a viscosity less than ~1 Pa s at a shear rate of ~100 s$^{-1}$) for facile application through high gauge needles. These properties enable minimally invasive implantation in vivo though direct injection or catheter-based delivery, providing for their use for controlled drug delivery.

Figure 2A:
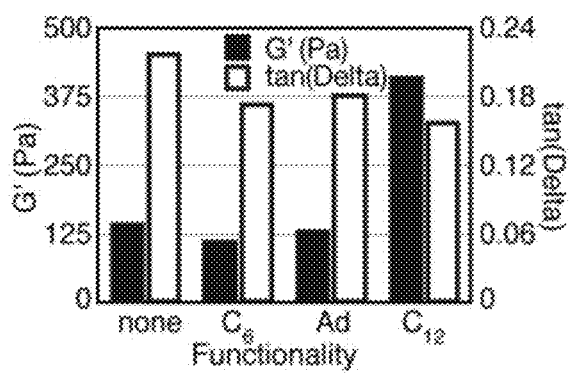
FIGS. 2a-l are graphs showing the rheological characterization of physically crosslinked hydrogels from HPMC derivatives and nanoparticles.
Figure 11:
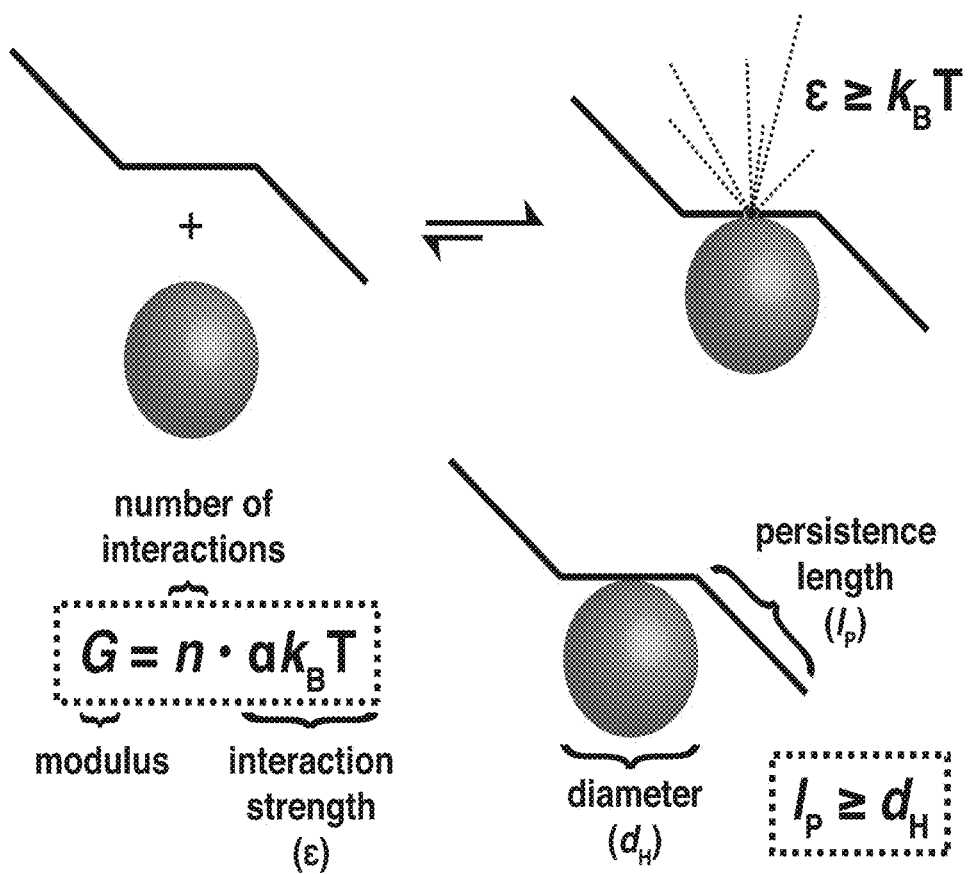
FIG. 11 is a diagram depicting polymer bridging of NPs (as opposed to polymer wrapping around individual particles).
Figure 12A:
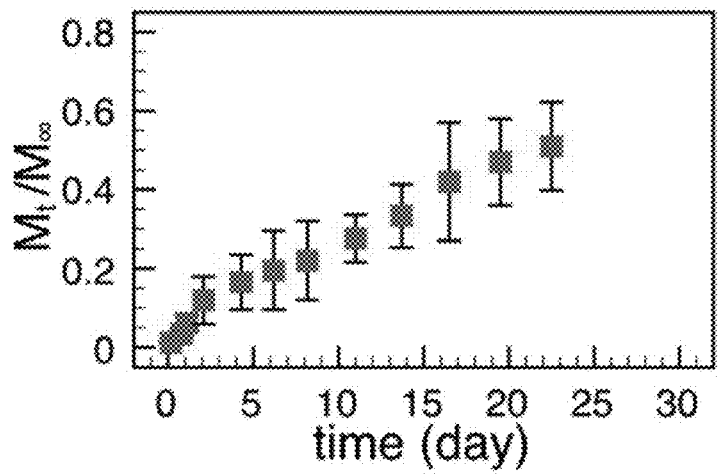
FIGS. 12a-b FIG. 12a is a graph of BSA release from HPMC-C12 (0.75%), MC (0.25%), and PEG-PLA NPs (10%) with a diffusional release coefficient of k=5.3%/day.
Figure 12B:
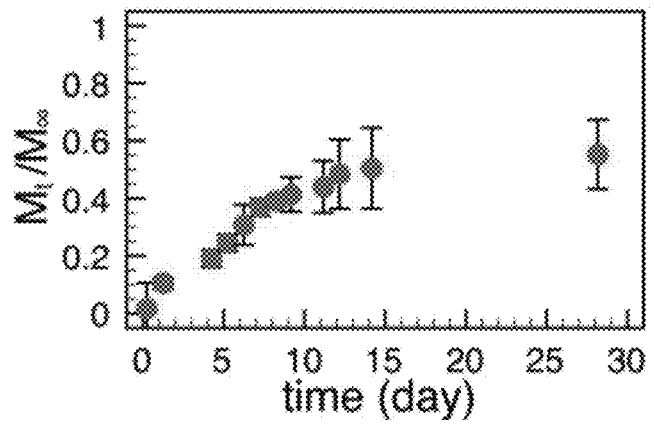

As a non limiting example of the present invention, PNP gel networks were formed by mixing aqueous solutions of a cellulose based polymer such as, for example, but not limited to, HPMC (Mn of about 700 kDa) and commercially available nanoparticles, such as, for example, but not limited to carboxy-functionalized polystyrene NPs (PSNPs; Dx of about 50 nm; 1 wt % HPMC: 10 wt % PSNPs) under ambient conditions (FIG. 2a). Such gels form rapidly upon mixing and exhibit a shear storage modulus of G'=140 Pa. Storage modulus (G') can be used as a measure of hydrogel strength, and tan delta, which is the ratio of the loss modulus (G") over the storage modulus (tan delta=G"/G'), can be used as a measure of hydrogel elasticity. Cellulosic biopolymers, such as, for example, but not limited to, HPMC, was chosen as the primary polymer for preparation of PNP gel networks on account of its high solubility, molecular weight, functionality and biocompatibility. PSNPs enabled a systematic investigation of the effect of NP number and NP diameter ($D_H$ approximately 50 nm to 500 nm), with uniform surface properties, on PNP gel network formation. Hydrogel formation is exclusive to the presence of both nanoparticles and gel forming biopolymers as nanoparticles (at 10 wt %) and gel forming biopolymers (at 1 wt %) solutions alone are each low viscosity liquids. Cryogenic transmission electron microscopy (TEM) indicates that the NPs remain homogeneously dispersed in the biopolymer continuous phase, suggesting that gel formation is driven by PNP interactions and not agglomeration (FIG. 11). Moreover, combining a biopolymer such as HPMC with commercially available silica NPs (Ludox TM-50; Dx of approximately 22 nm; 1 wt % HPMC: 10 wt % NPs) failed to form a gel. These data indicate that selective adsorption of biolpolymer chains such as HPMC chains to NPs results in multivalent interactions including crosslinking and gel formation.

Efficient crosslinking necessitates strong affinity between the NPs and the polymer chains, that is, the free energy gain (c) resulting from adsorption of a polymer chain to the surface of a NP should be greater than or comparable to the thermal energy ($k_BT$). In addition, the average number of interactions per polymer chain and particle must be >2 to achieve percolation of the network. Moreover, to favor polymer bridging of multiple NPs (as opposed to polymer wrapping around individual particles), the NP diameter should be comparable to, or less than, the persistence length ($l_P$) of the polymer strands (see FIG. 11). When these criteria are met, NPs are able to serve as crosslinkers between the polymer chains, while the polymer chains may bridge many different particles, enabling hydrogel formation. From polymer physics, the modulus (G) of PNP hydrogels can be related to the number of PNP interactions per unit volume (n) and the energy associated with each interaction ($\alpha k_BT$) using theoretical tools analogous to those developed for covalent hydrogels: G≈n $\alpha k_BT$ (Rubinstein, M. & Colby, R. H. Polymer Physics Oxford Univ. Press, 2003).

Hydrophobic modification of polymers such as, but not limited to, HPMC (yielding HPMC-x) increases the energy associated with each polymer nanoparticle interaction ($\alpha k_BT$), thereby increasing the modulus of the PNP gel network given the same number of interactions per unit volume. Such modification facilitates favorable interactions between the hydrophobic moiety on the polymer chain such as the HPMC chain and the hydrophobic core of the nanoparticle such as PSNP, thereby enhancing the adsorption energy of the biopolymer such as HPMC to the NPs. Cellulosic gel forming polymers, such as but not limited to, HPMC can readily functionalized using commercially available Michael acceptors such as for example, but not limited to, isocyanates (including hexyl, adamantyl and dodecyl isocyanate); in a one-step reaction performed at ambient temperature using dibutyltin dilaurate (TDL) as a catalyst (see Scheme 1).

Scheme 1

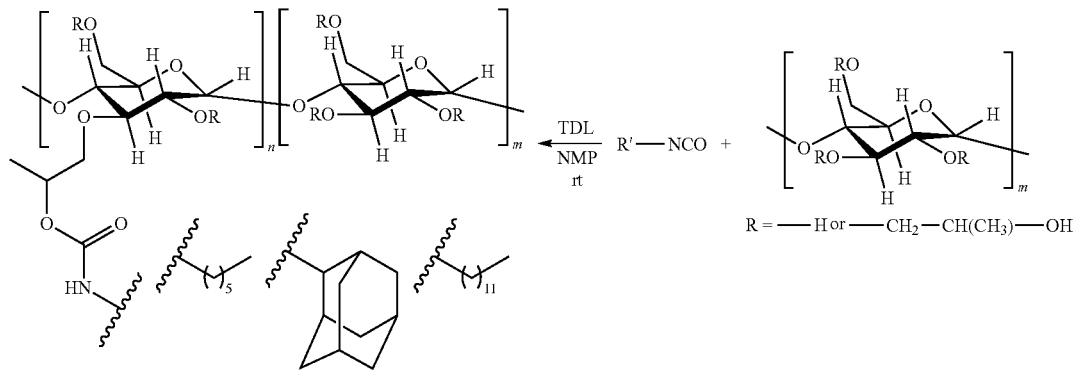

PNP gel networks were subsequently made using modified gel forming polymer and nanoparticle, and in the case of HPMC, the PNP gel network comprises the structure HPMC-x, wherein x refers to hexyl ($C_6$), adamantyl (Ad) or dodecyl (Cu) functionality, and NPs ($D_H$ of about 50 nm; 1 wt % HPMC-x: 10 wt % PSNPs). PNP gel networks formed with either HPMC-$C_6$ or HPMCAd possessed similar properties to unmodified HPMC gels. However, PNP gels formed with HPMC-$C_{12}$ were roughly three times stronger (G' about 400 Pa), indicating an increased interaction energy between the Cu moieties and the PSNPs (FIG. 2a; Supplementary FIG. 2). The rheology of the HPMC-$C_{12}$ polymer at 1 wt % is equivalent to the non-functionalized HPMC, despite conjugation of hydrophobic moieties (Supplementary FIG. 3) and the polymer's ability to form hydrogels at higher concentrations. In some embodiments of the PNP gels the viscosity is less than 1 Pa s at a shear-rate of ~100 s$^{-1}$. In some embodiments, the PNP gels have a shear storage modulus of G' of between about 5 Pa and about 100,000 Pa.

In other embodiments, the shear storage modulus (G') is between about 100 Pa and about 10,000 Pa. In other embodiments, the shear storage modulus (G') is between about 500 Pa and about 5,000 Pa. In still other embodiments, the shear storage modulus (G') is between about 1,000 Pa and about 2,500 Pa In some embodiments, the PNP gel has an elasticity of between about 10 Pa and about 10,000 Pa. In some embodiments, the PNP gel has an elasticity of between about 100 Pa and about 1,000 Pa. In some embodiments, the PNP gel has an elasticity of between about 200 Pa and about 500 Pa.

Figure 2B:
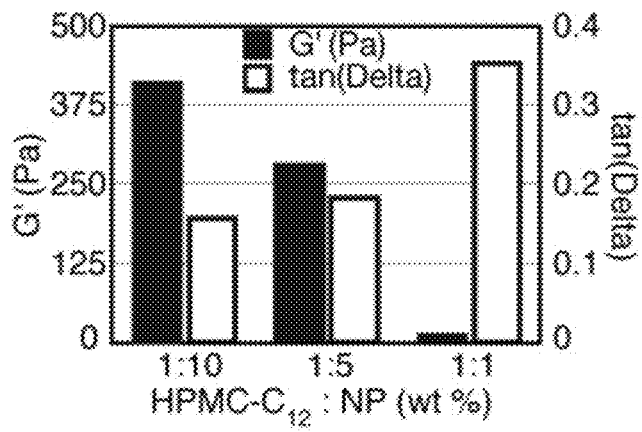

NP number and size effect PNP gel formation. Gel modulus scales directly with the number of NPs and particle sizes below a critical diameter, expected to be comparable to the persistence length of the polymer ($l_P$ of about 90 nm for HPMC) facilitates bridging between particles, thus facilitating gel network formation. The number of NPs in the PNP gel network can be modulated by formulating PNP solutions with decreasing fractions of NPs (1 wt % HPMC-$C_{12}$: and either 10 wt %, 5 wt %, or 1 wt % NPs with $D_H$ of about 50 nm). The shear storage modulus (G') decreased with fewer NPs, and consequently decreasing number of PNP interactions per unit volume (n; FIG. 2b).

A. Nanoparticles

The PNP gel networks described herein comprise particles, such as, for example nanoparticles. Generally, the nanoparticles are made from polymers using conventional chemistries. The nanoparticles may contain biodegradable polymers. Suitable biodegradable polymers include, but are not limited to, synthetic polymers such as, for example, but not limited to, polyhydroxy acids, such as polymers of lactic acid and glycolic acid, polyanhydrides, poly(ortho)esters, polyesters, polyurethanes, poly(butic acid), poly(valeric acid), poly(caprolactone), poly(hydroxybutyrate), poly(lactide-co-glycolide), poly(lactide-co-caprelactone), poly(ethylene-co-maleic anhydride), poly(ethylene maleic anhydride-co-L-dopamine), poly(ethylene maleic anhydride-co-phenylalanine), poly(ethylene maleic anhydride-co-tyrosine), poly(butadiene-co-maleic anhydride), poly(butadiene maleic anhydride-co-L-dopamine) (pBMAD), poly(butadiene maleic anhydride-co-phenylalanine), poly(butadiene maleic anhydride-co-tyrosine), as well as blends comprising these polymers; and copolymers comprising the monomers of these polymers. Naturally occurring biodegradable polymers include polysaccharides such as, for example, but not limited to, alginate, collagen, chitosan, gelatin, hyaluronic acid, proteins such as, for example, but not limited to, fibrin, albumin, and zein, as well as chemically modified derivatives of naturally occurring polymers, and mixtures thereof. Generally, these materials degrade either by enzymatic hydrolysis or exposure to water in vivo, by surface or bulk erosion.

The nanoparticles may contain non-biodegradable polymers. In some embodiments, the intended uses of the shear-thinning PNP gel are biomedical in nature. In such embodiments, the non-biodegradable polymers are biocompatible. Suitable non-biodegradable polymers include, but are not limited to, polystyrenes, polyalkylene glycols, poly (meth)acrylates, poly (meth)acrylamides, polyalkylenes such as, for example, but not limited to, polyethylene, polyvinyls, poly(vinyl acetate), poly(ethylene terephthalate), as well as blends comprising these polymers, and copolymers of these polymers.

In certain embodiments, the nanoparticle is a core-shell particle. The core and the corona (the shell) may be made from separate polymeric materials, or may be made from a single block-copolymer, wherein one block of the polymer forms the core while another block forms the shell. In another embodiment, one or both of the components of the core-shell is a non-polymeric material. The core shell particle is composed of two compositionally disparate phases, of which one (either the core or corona) is hydrophobic and the other (core or corona) is hydrophilic.

Suitable hydrophobic components can include, but are not limited to, polyamides, including poly (amino acids), polyesters, such as, for example, but not limited to, polylactic acid, polypropylene oxides, polystyrenes, and mixture thereof.

Suitable hydrophilic components can include, but are not limited to, polysaccharides, proteins, polyamides, including poly (amino acids), naturally occurring polymers, synthetic polymers, and combinations thereof.

Suitable block copolymers include combinations of polyethylene glycol and polyesters, such as, for example, but not limited to, poly(lactic acid), combinations of polyethylene glycol and polypropylene glycol (i.e., polaxomers).

The molecular weight of the polymer or polymers can vary. Suitable molecular weight ranges for nanoparticle formations are about 500 Daltons to about 10,000,000 Daltons. In some embodiments, the molecular weight ranges for nanoparticle formations are about 1,000 Daltons to about 1,000,000 Daltons. In some embodiments, the molecular weight ranges for nanoparticle formations are about 10,000 Daltons to about 100,000 Daltons.

The size of the particles can vary. In some embodiments the particle size is from about 10 nm to about 1,000 nm. In other embodiments, the particle size is from about 10 nm to about 500 nm. In other embodiments, the particle size is from about 10 nm to about 250 nm. In other embodiments, the particle size is from about 10 to about 150 nm. In some embodiments, the particle size is about 10 nm, about 20 nm, about 30 nm, about 40 nm, about 50 nm, about 60 nm, about 70 nm, about 80 nm, about 90 nm, about 100 nm, about 110 nm, about 120 nm, about 130 nm, about 140 nm, or about 150 nm.

In some embodiments, the particle material may be of an inorganic composition, such as, for example, but not limited to, clays, such as, for example, but not limited to, silicates, minerals, including sulfides, oxides, halides, carbonates, sulfates, and phosphates thereof, as well as other minerals and apatites. The particle may also be made of one or more metals, such as, for example, but not limited to, gold, silver, copper, platinum, palladium, and ruthenium.

In some embodiments, the particle material may be carbon nanotubes, including both single-walled and multi-walled nanotubes, graphene, graphene oxide, or other ultrathin single crystals, including black phosphorous and boron based nanosheets.

In some embodiments, the particle material may be cellulose nanocrystals or cellulose nanofibers.

In some embodiments, the NP can be at a concentration of between about 1 wt % to about 15 wt %. In some embodiments, the NP can be at a concentration of between about 2 wt % to about 12 wt %. In some embodiments, the NP can be at a concentration of between about 3 wt % to about 10 wt %. In some embodiments, the NP can be at a concentration of between about 5 wt % to about 8 wt %. In some embodiments, the NP can be at a concentration of about 1 wt %, about 2 wt %, about 3 wt %, about 4 wt %, about 5 wt %, about 6 wt %, about 7 wt %, about 8 wt %, about 9 wt %, about 10 wt %, about 11 wt %, or about 12 wt %.

B. Continuous Phase

The PNP gel network forms when the nanoparticles described above are mixed with and interact with a continuous phase. The shear-thinning and self-healing properties of the PNP gel network are derived from reversible, non-covalent interactions between the nanoparticles and continuous phase. The continuous phase may contain a variety of gel-forming materials, including but not limited to, polysaccharides, proteins, naturally occurring polymers, synthetic polymers, and combinations thereof.

Exemplary proteins include, but are not limited to, collagen, gelatin, and fibrin.

Exemplary polysaccharides include, but are not limited to, starch, alginate, agarose, cellulosic derivatives, such as, for example, but not limited to, hydroxypropyl methyl cellulose (HPMC), carboxymethyl cellulose (CMC) and n-ethyl cellulose, hyaluronic acid, chitosan, xanthan gum, and agar.

Exemplary synthetic polymers include, but are not limited to, polyacrylamide, polylactic acid (PLA), polyethylene glycol (PEG), polyethylene glycol-co-propylene glycol (PEO-PPO), and pol) acrylates, such as, for example, but not limited to, poly(2-hydroxyethylmethacryiate).

The shear-thinning and self-healing properties of the network may be adjusted by chemical modification of the gel-forming polymers described above. In certain embodiments, gel-forming polymers that contain reactive functional groups (e.g., hydroxyl, amino, carboxyl, thiol, and the like) may be derivatized with one or more capping groups. Suitable capping groups include, but are not limited to, $C_1$-$C_{20}$ alkyl groups, $C_3$-$C_{18}$ cycloalkyl groups, and $C_6$-$C_{18}$ aryl groups. These groups may be unsubstituted or substituted one or more times. Exemplary substituents include halogen (F, Cl, Br, I), —NO2, —CN, —OH, —NH2, —COOH, —SO$_3$H, —PO$_3$H$_2$, and salts thereof. The trapping groups may be attached to the gel-forming polymer using conventional chemistries. For instance, polymers containing nucleophilic functional groups may be reacted with activated carboxylic acid derivatives (acid chlorides, anhydrides, reactive esters and the like), isocyanates, epoxides, alkyl halide, alkyl sulfonate esters, and other electrophilic functional groups to prepare ester, carbonate, amide, carbamate, urea, ether or amine-linked capping groups. In other embodiments, polymers containing carboxyl functional groups may be esterified or amidated in order to modify their overall hydrophilicity.

In certain embodiments of hydrophobically-modified gel-forming polymers, the capping group contains at least 6 carbons. In other embodiments they contain at least 8 carbons. In other embodiments they contain at least 10 carbons. In other embodiments they contain at least 12 carbons. In some embodiments they contain linear alkyl groups, such as, for example, but not limited to, n-dodecyl, n-decyl, n-octyl. In other embodiments, cyclic alkyl groups such as, for example, but not limited to, cyclohexyl, adamantly or decalinyl may he used. Suitable aryl groups includes phenyl, naphthalyl, anthracenyl and phenanthracenyl.

Without wishing to be bound to any particular theory, it is believed that the non-covalent interaction between the nanoparticle and the modified gel-forming polymer contributes to the shear-thinning and self-healing nature of the composition. That is to say, the non-covalent interactions between the nanoparticle and the gel-forming polymer allow the stretching of the PNP gel network under applied strain and upon removal of the strain the multivalent interactions contract the PNP gel network (self-healing). Thus, the physical properties of the hydrogel may be tuned by appropriate selection of functional groups on the hydrophilic polymer and nanoparticle. For instance, under in vivo conditions, ester containing capping groups will degrade more rapidly than capping groups attached via amide or other such bond. The strength of the non-covalent interactions between the gel-forming material and nanoparticle will depend, in part, on the surface area and polarization of the hydrophobic capping groups.

C. Enhancers

The interaction between polymers and nanoparticles can be enhanced by other enhancer compounds that provide, for example, bridging type non covalent interactions between polymers and nanoparticles. In particular, a portion of an enhancer compound can interact noncovalently with the polymer and a second portion of the enhancer compound can interact with the nanoparticle. Non limiting examples of such interactions include ionic interactions such as cationic/anionic interactions, electrostatic interactions, and hydrogen bonding interactions. In some embodiments, polymers are anionically charged at physiological pH, and thus provide ionic interactions which can facilitate polymer-nanoparticle interactions leading to gel formation. The selective adsorption of negatively charged polymers, such as for example, but not limited to, hyaluronic acid (HA) and carboxymethylcellulose (CMC), to nanoparticles comprising poly(ethylene glycol)-b-poly(lactic acid) (PEG-b-PLA) is enhanced with a positively charged surfactant, such as for example, but not limited to, cetyltrimethylammonium bromide (CTAB), cetyltrimethylammonium iodide, cetyltrimethylammonium fluoride, or cetyltrimethylammonium chloride. In one embodiment the enhancer is CTAB. In other embodiments, polymers are cationically charged, and the selective adsorption of positively charged polymers, such as for example, but not limited to, chitosan, aminopolysaccharides, positively charged proteins such as but not limited to polylysine, cationic polymers such as cationic acrylate polymers, and cationic vinyl polymers to nanoparticles is enhanced with a negatively charged surfactant, such as for example, but not limited to, sodium dodecyl sulfate, sodium stearate and charged fatty acid surfactants. In other embodiments, molecular recognition between at least two compounds can provide the enhancement. For example, the adsorption of polymers such as polysaccharides to nanoparticles can be enhanced by an enhancer compound which comprises both a carbohydrate in one portion of the enhancer and a polymer tail that interacts with the nanoparticle.

Figure 7:
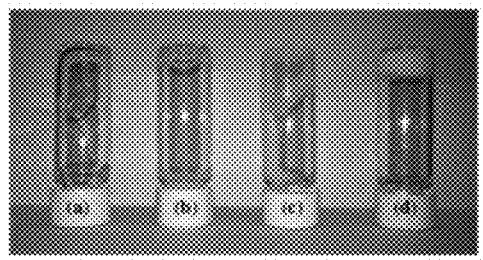
FIG. 7 shows an inverted vial test of PNP hydrogels exploiting electrostatic interactions between non-functionalized, anionic polymers and NPs in the presence of cetyl trimethylammonium bromide (CTAB): (a) CMC (1%), (b) NPs (10%), (c) CMC (1%)+NPs (10%), and (d) CMC (1%)+NPs (10%)+CTAB (0.25%).

In one non limiting example, the addition of a cationic surfactant molecule imparts sufficient interaction strength between the anionic biopolymers (via electrostatic interactions) and the core-shell nanoparticles (via hydrophobic interactions). Combining a solution of an anionically charged biopolymer such as, for example, CMC (3%) and CTAB (1.5%) with a nanoparticle such as, for example, PEG-b-PLA NPs (15%) followed by vigorous mixing affords a final concentration of CMC:NP:CTAB (1:10:0.5). The interaction between the CMC polymer and the NPs alone is not sufficiently strong to induce gel formation, and gels are formed exclusively when all three components are present (FIG. 7).

D. Effects of the CTAB on Gel Formation

Figure 8A:
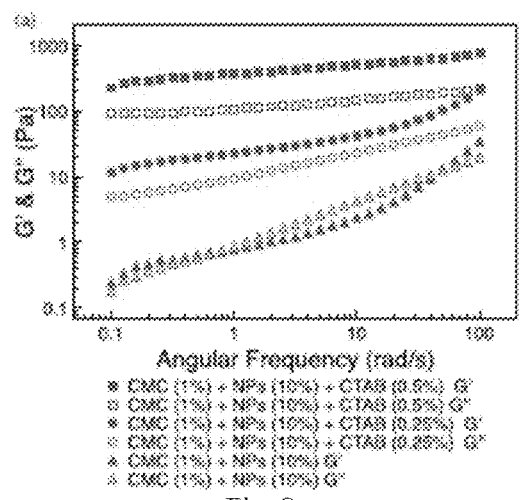
FIGS. 8a-b show a frequency-dependent oscillatory rheological characterization (g=2%) of PNP hydrogels comprising (a) CMC and (b) HA.
Figure 8B:
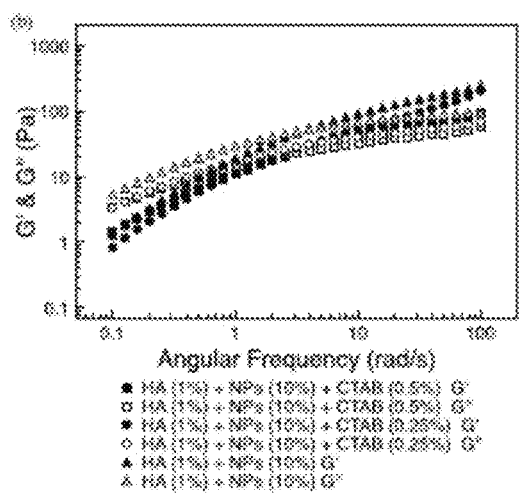

Combinations of HA/CTAB and NPs and CMC/CTAB and NPs were prepared with varying concentrations of CTAB present and characterized (FIGS. 8a and 8b). The frequency dependence of the storage and loss oscillatory shear moduli (G' and G", respectively), are shown in FIG. 8a and both are linear and parallel and G' is dominant across the whole range of frequencies observed. In general, these CMC/CTAB—NP hydrogels are soft (G'≈0.5 kPa at 0.5% loading of CTAB), yet are highly elastic (tan d=G"/G'≈0.2). Moreover, the mechanical properties of the material can be tuned over several orders of magnitude simply through alteration of the formulation. The combination of HA/CTAB and NPs exhibit viscoelastic behavior, where the crossover of G' and G" is observed at frequencies around 2 rad/s.

E. Mixed Polymer Systems

Figure 9:
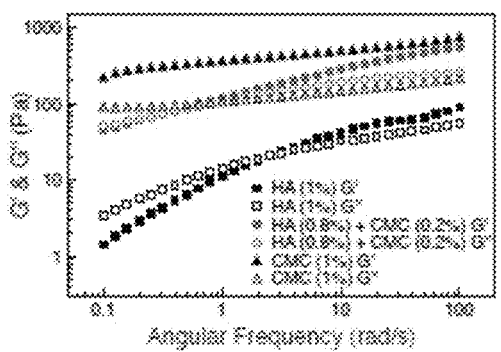
FIG. 9 shows a freqency-dependent oscillatory rheological characterization (g=2%) of PNP hydrogels prepared from HA, CMC, NPs (10%), and CTAB (0.5%). The modular electrostatic interactions responsible for crosslinking allow for facile alteration of mechanical properties via modulation of the formulation.
Figure 10A:
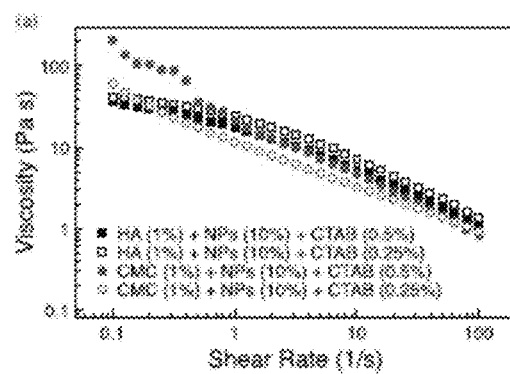
FIGS. 10a-b show a flow rheological characterization of PNP hydrogels: (a) steady-shear measurements and (b) step-rate time-sweep measurements displaying recovery of hydrogel structure at low shear rate (g·$0.1\ s^{-1}$) following high-magnitude deformation (g·$100\ s^{-1}$). Fitting of viscosity recovery following to a single-stage association model ($R2>0.98$) yields a characteristic time ($t_R$) for recovery of hydrogel structure (inset; n=3).
Figure 10B:
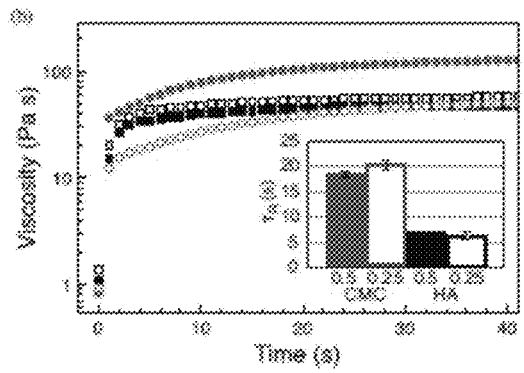

Mixed-polymer gel forming systems with both HA and CMC were prepared and their non-covalent interactions and their amenability to combinatorial mixing were investigated. FIG. 9 demonstrates materials prepared from HA (0.8%), CMC (0.2%), CTAB (0.5%), and NPs (10%) exhibit intermediate properties between those of materials prepared with CMC or HA alone. Thus, materials composed primarily of HA can be prepared with significantly enhanced mechanical properties (i.e. greater than one order of magnitude increase in G') by simple addition of a small proportion of CMC into the formulation. Additionally, strain-dependent oscillatory rheology (see supporting information) of the materials formed from PEG-PLA NPs (10%), HA or CMC (1%), and CTAB (0.25 or 0.5%) demonstrates an extremely broad linear viscoelastic region, indicating that these materials have an extensive processing region. The relative loadings of CTAB and the various biopolymers used can produce materials with a large range of mechanical properties. Flow rheological measurements of HA and CMC containing PNP gel networks show that they are shear-thinning (i.e., viscosity decreases from ~100 Pa s to ~1 Pa s as the shear rate increases from ~0.1 $s^{-1}$ to ~100 $s^{-1}$) (FIG. 9a). Moreover, these materials also exhibit a nontrivial difference in viscosity in the low-shear regime (i.e., shear rate of ~0.1 $s^{-1}$), whereby higher CTAB loading corresponds to a roughly 2.5× increase in viscosity, while the viscosity of these materials in the high-shear regime (i.e., shear rate of ~100 $s^{-1}$) is independent of the CTAB concentration. FIG. 5b clearly demonstrates the exceptionally fast and complete recovery of viscosity after destruction of the gel structure in a matter of a few seconds.

F. Therapeutic, Prophylactic, and Diagnostic Agents

The PNP gel networks are amenable to a range of biomedical applications, including injectable drug delivery systems, cell carriers for tissue engineering, and bone fillers. Due to the biphasic nature of the hydrogel, release of hydrophilic drugs is controlled by Fickian diffusion, while hydrophobic drugs are released by gel erosion, affording differential release rates of multiple compounds from a single material, both in vitro and in vivo. Thus, multiple therapeutic agents can be encapsulated into the same gel, yet released over different time periods with different rates.

The compositions can contain one or more therapeutic, prophylactic and/or diagnostic agents. The agent can be organic, inorganic, or organometallic. The agent can be a small molecule, e.g., molecular weight less than 2000, 1500, 1000, 750, or 500 Dalton or a macromolecule, e.g., molecular weight greater than 2,000 Daltons, such as proteins, enzymes, etc.

Exemplary therapeutic agents that can be incorporated into the particles/hydrogel include, but are not limited to, tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasitics (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of the particles into cells (including dendritic cells and other antigen-presenting cells), nutraceuticals such as vitamins, and oligonucleotide drugs (including DNA, RNAs, antisense, aptamers, small interfering RNAs, ribozymes, external guide sequences for ribonuclease P, and triplex forming agents).

Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®). Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

Examples of immunological adjuvants that can be associated with the particles include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A.

The particles/hydrogel may also include antigens and/or adjuvants (i.e., molecules enhancing an immune response). Peptide, protein, and DNA based vaccines may be used to induce immunity to various diseases or conditions. Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA based vaccines are potentially safer than traditional vaccines. DNA vaccines are relatively more stable and more cost-effective for manufacturing and storage. DNA vaccines consist of two major components—DNA carriers (or delivery vehicles) and DNAs encoding antigens. DNA carriers protect DNA from degradation, and can facilitate DNA entry to specific tissues or cells and expression at an efficient level.

Exemplary diagnostic agents include paramagnetic molecules, fluorescent compounds, magnetic molecules, and radionuclides, x-ray imaging agents, and contrast agents.

In some embodiments, the compositions described herein contain less than 80%, less than 75%, less than 70%, less than 60%, less than 50% by weight, less than 40% by weight, less than 30% by weight, less than 20% by weight, less than 15% by weight, less than 10% by weight, less than 5% by weight, less than 1% by weight, less than 0.5% by weight, or less than 0.1% by weight of the agent. In some embodiments, the agent may be a mixture of pharmaceutically active agents. The percent loading is dependent on a variety of factors, including the agent to be encapsulated in the particles and/or dispersed within the gel, the polymer used to prepared the particles and/or the gfel, and/or the method used to prepare the particles/gel.

The one or more agents can be encapsulated within the particles, associated with the surface of the particles (e.g., covalently or non-covalently) and/or be dispersed through the hydrogel.

III. Methods of Making the Compositions

A. Nanoparticles

Nanoparticles, including core-shell particles, can be prepared using techniques known in the art. The technique to be used can depend on a variety of factors including the polymer used to form the nanoparticles, the desired size range of the resulting particles, and suitability for the material to be encapsulated. Suitable techniques include, but are not limited to:

1. Solvent Evaporation

In this method the polymer is dissolved in a volatile organic solvent. The drug (either soluble or dispersed as fine particles) is added to the solution, and the mixture is suspended in an aqueous solution that optionally contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method.

2. Hot Melt Microencapsulation

In this method, the polymer is first melted and then mixed with the solid particles. The mixture is suspended in a non-miscible solvent (like silicon oil), and, with continuous stirring, heated to 5° C. above the melting point of the polymer. Once the emulsion is stabilized, it is cooled until the polymer particles solidify. The resulting nanoparticles are washed by decantation with petroleum ether to give a free-flowing powder. The external surfaces of spheres prepared with this technique are usually smooth and dense.

3. Solvent Removal

In this method, the drug is dispersed or dissolved in a solution of the selected polymer in a volatile organic solvent. This mixture is suspended by stirring in an organic oil (such as silicon oil) to form an emulsion. Unlike solvent evaporation, this method can be used to make nanoparticles from polymers with high melting points and different molecular weights. The external morphology of spheres produced with this technique is highly dependent on the type of polymer used.

4. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried.

5. Phase Inversion

Nanospheres can be formed from polymers using a phase inversion method wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. The method can be used to produce nanoparticles in a wide range of sizes, including, for example, about 100 nanometers to about 10 microns. Substances which can be incorporated include, for example, imaging agents such as fluorescent dyes, or biologically active molecules such as proteins or nucleic acids. In the process, the polymer is dissolved in an organic solvent and then contacted with a non-solvent, which causes phase inversion of the dissolved polymer to form small spherical particles, with a narrow size distribution optionally incorporating an antigen or other substance.

Other methods known in the art that can be used to prepare nanoparticles include, but are not limited to, polyelectrolyte condensation (see Suk et al., *Biomaterials*, 27, 5143-5150 (2006)); single and double emulsion (probe sonication); nanoparticle molding, and electrostatic self-assembly (e.g., polyethylene imine-DNA or liposomes).

B. Polymer-Nanoparticle (PNP) Gel Compositions

In some embodiments, the compositions are prepared by dissolving the continuous phase in a first solvent, such as water, with heating if necessary to form a first solution. The nanoparticles are then dissolved in the same solvent or a second solvent to form a second solution. The two solutions are then combined, optionally with external agitation, to form the PNP gel compositions.

Throughout this disclosure, various publications are referenced. The disclosures of these publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

C. Examples

Rheological characterization was performed using a TA Instruments AR-G2 controlled stress rheometer fitted with a Peltier stage. All measurements were performed using a 40 mm 2 cone geometry and analyzed using TA Instruments TA Orchestrator software.

CryoSEM images where acquired using a Zeiss NVision 40 (Carl Zeiss SMT, Inc.) field emission scanning electron microscope at an acceleration voltage of 2 kV. CryoTEM images where acquired using a JEOL 2100 FEG microscope (Jeol Inc. Peabody, Mass.) equipped with a Gatan 2kx2k UltraScan CCD camera at an acceleration of 200 kV and at magnification ranges of 10,000-30,000×.

1. Example 1. PEG-b-PLA Synthesis

Polyethylene glycol (PEG, 0.25 g, 4.1 mmol) and 1,8-diazabicycloundec-7-ene (DBU; 10.6 mg, 10 µL, 1.0 mol % relative to LA) were dissolved in dichloromethane (DCM, 1.0 mL). Lactide (LA; 1.0 g, 6.9 mmol) was dissolved in DCM (3.0 mL) with mild heating. The LA solution was added rapidly to the PEG/DBU solution and stirred rapidly for 10 minutes. The reaction mixture was quenched by the addition of acetone (7.0 mL) and the PEG-block-PLA (PEG-b-PLA) copolymer was recovered by precipitation from cold diethyl ether, collected by filtration, and dried under vacuum to yield a white amorphous polymer (1.15 g, 92%). GPC (THF):Mn (PDI)=25 kDa (1.09).

2. Example 2. PEG-b-PLA Nanoparticle (NP) Preparation

A solution of PEG-b-PLA in DMSO (40 mg/mL) was added dropwise to water (10× v/v) under a high stir rate. NPs were purified by ultracentrifugation over a filter (MWCO 30 kDa) followed by resuspension in water to a final concentration of 150 mg/mL. NP size and dispersity were characterized by dynamic light scattering (DLS) with a Malvern Zetasizer Nano-ZS.

Example 3. HPMC-$C_{12}$ (n-dodecyl-capped HPMC) Preparation

HPMC was functionalized using dodecyl isocyanate in a one-step reaction performed at ambient temperature in N-methylpyrrolidone using dibutyltin dilaurate (TDL) as a catalyst. The reaction solution was then precipitated from acetone and the polymer was recovered by filtration and dried under vacuum. Using the same protocol, hexyl HPMC (HMPC-$C_6$) and adamantyl HPMC (HMPC$_{adm}$) were also prepared.

3. Example 4. Polymer-Nanoparticle (PNP) Gel Preparation

PNP gels were prepared by first dissolving hydroxypropylmethyl-cellulose (HPMC) polymers in water (30 mg/mL) with stirring and mild heating. Nanoparticles were either purchased or prepared according to literature procedures and were concentrated to 15 wt % solutions. HPMC polymer solution (150 µL) and NP solution (300 µL) were then added together and mixed well by vortex (some samples were mildly centrifuged to remove bubbles arising from mixing). The process is show schematically in FIG. 1.

An aqueous solutions of hydroxypropylmethylcellulose (HPMC; Mn~700 kDa) and commercially available carboxy-functionalized polystyrene nanoparticles (PS-COOH NPs; d~50 nm; 1 wt % HPMC: 10 wt % NPs) under ambient conditions. These gels formed rapidly upon mixing, exhibiting a shear storage modulus of G'=140 Pa. By the same methods PNP hydrogel made from HPMC-$C_{12}$ and PEG-b-PLA NPs was prepared.

PNP gels formed with either HPMC-$C_6$ or HPMC$_{Adm}$ possessed similar properties to unmodified HPMC gels. However, PNP gels formed with HPMC-$C_{12}$ were roughly three times stronger (G'=400 Pa), indicating an increased interaction energy between the $C_{12}$ moieties and the core-shell PS-COOH NPs (FIG. 2a).

The number of nanoparticles in the PNP gels was modulated by formulating PNP solutions with decreasing fractions of PS-COOH NPs (1 wt % HPMC-$C_{12}$:10, 5, or 1 wt % PS—COOH NPs with d~50 nm). The shear storage modulus (G') decreased with decreasing number of NPs, and consequently, decreasing number of polymer-nanoparticle interactions per unit volume (n) (FIG. 2b).

Figure 2C:
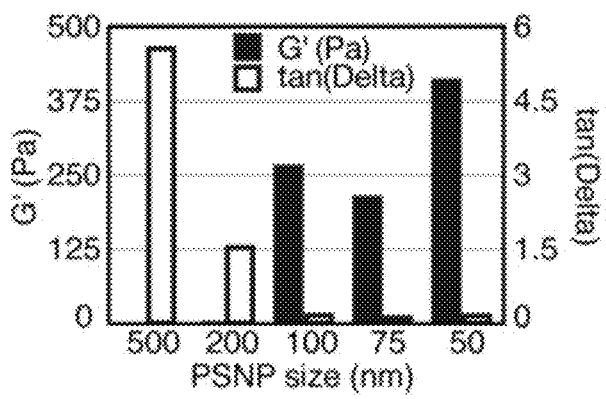

PNP gel formation was screened with PS-COOH NPs of various sizes (d~50 nm, 75 nm, 100 nm, 200 nm, and 500 nm; 1 wt % HPMC-$C_{12}$: 10 wt % NPs). It was observed that robust gels formed with particle diameters equal to or less than 100 nm, whereas larger particles failed to produce gels (FIG. 2c).

Figure 2D:
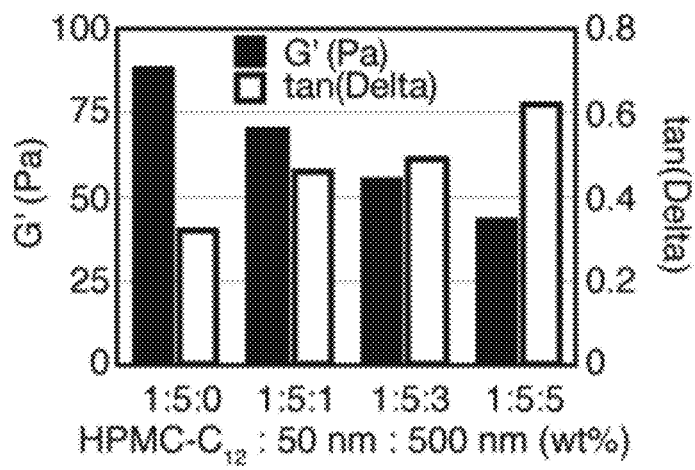
Figure 2E:
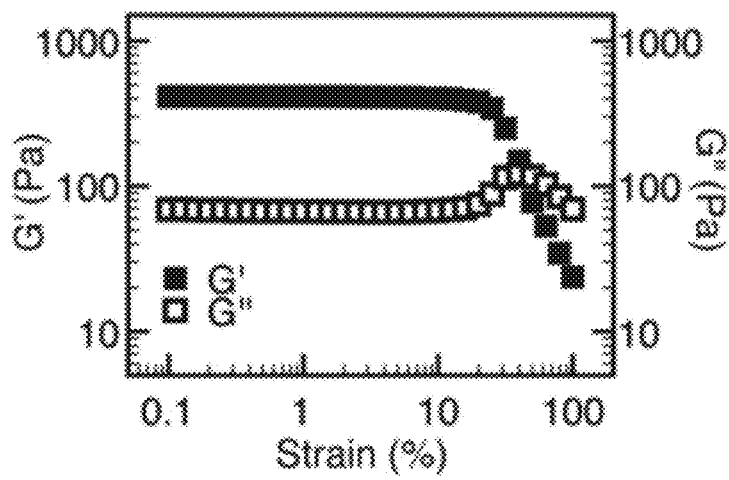

PNP gels composed of HPMC-$C_{12}$ (1 wt %) and both 50 nm PS—COOH NPs (5 wt %) and 500 nm PS—COOH NPs (1, 3 and 5 wt %) were formulated. As large particles are titrated into the PNP gels, a monotonic decrease in material properties was observed (FIG. 2d).

Figure 2F:
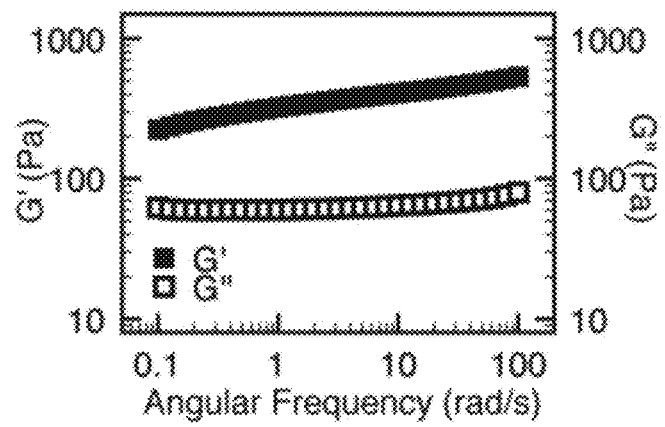
Figure 2G:
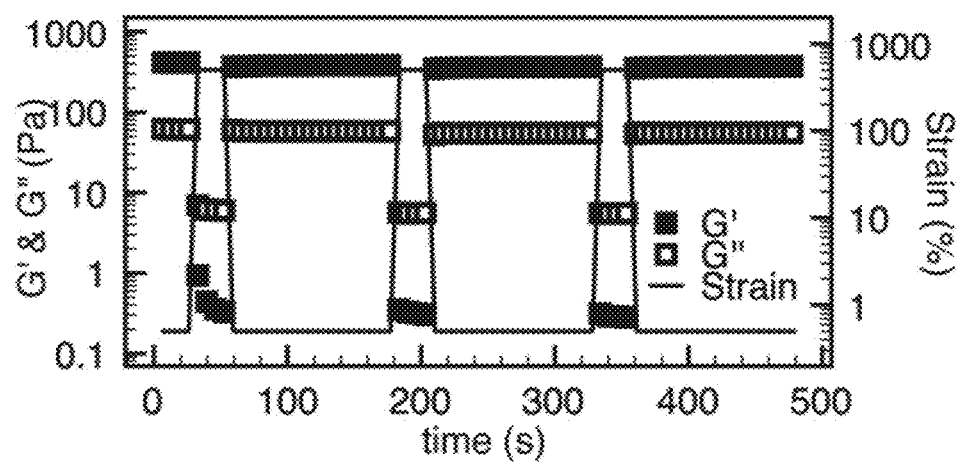
Figure 2H:
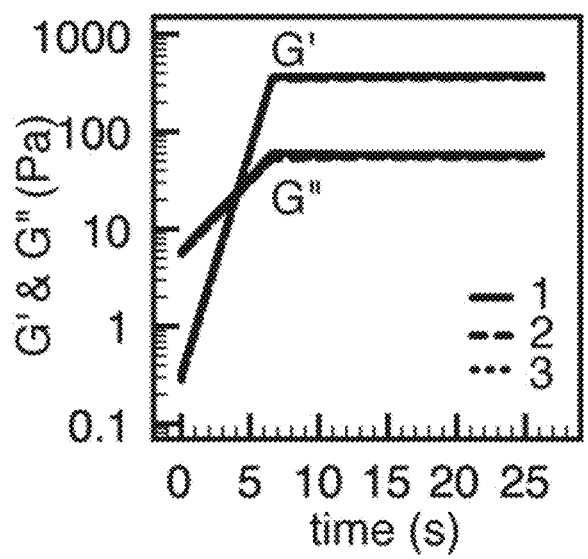

Strain dependent oscillatory rheology (FIG. 2e) of the HPMC-$C_{12}$ PNP gels (1 wt % HPMC-$C_{12}$: 10 wt % 50 nm PSCOOH NPs) displayed an extremely broad linear viscoelastic region in addition to network failure at high strains, indicating a wide processing regime and shear-thinning behavior. The frequency dependence of the storage and loss oscillatory shear moduli (G' and G", respectively) confirmed hydrogel-like behavior as G' is dominant across the whole range of frequencies observed (0.1-100 rad/s; FIG. 2f). Step-strain measurements were then performed to investigate the recovery of material properties following network rupture at high strains (a critical parameter for injectability). A high magnitude strain (γ=500%) was applied to break the hydrogel structure, followed by a low magnitude strain (γ=0.5%) to monitor the rate and extent of recovery of bulk properties (FIG. 2g). These materials exhibit exceptionally fast and complete recovery of properties in a matter of a few seconds after stress-induced flow. Moreover, the rate and extent of recovery is unchanged over several cycles of breaking and reforming, highlighting the reversible and robust nature of the non-covalently crosslinked hydrogel structure (FIG. 2h).

4. Example 5. PNP Hydrogels from Biodegradable NPs

Figure 2I:
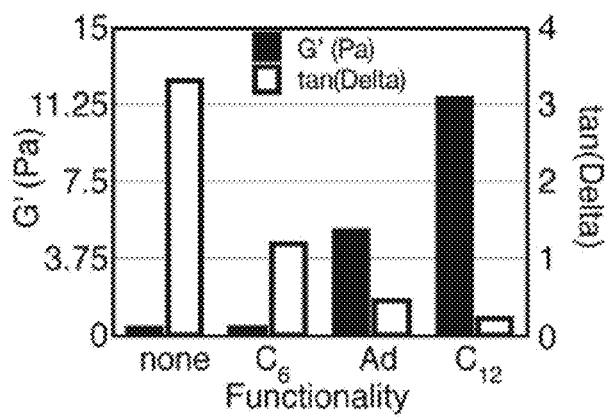
Figure 2J:
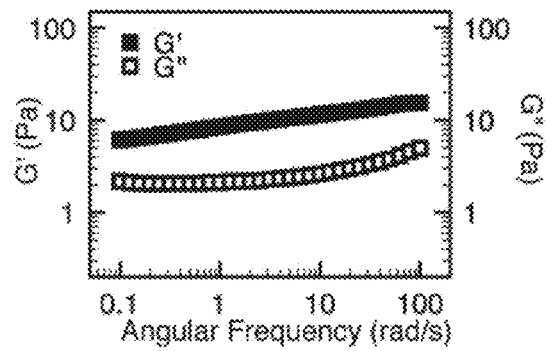
Figure 2K:
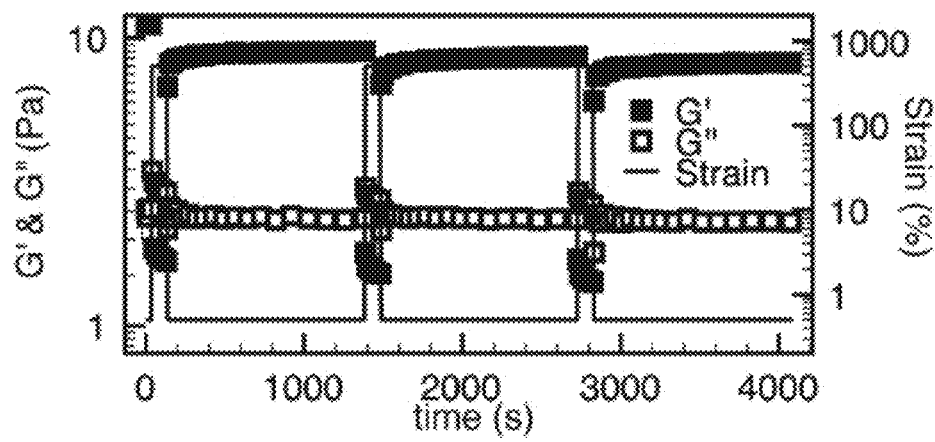
Figure 2L:
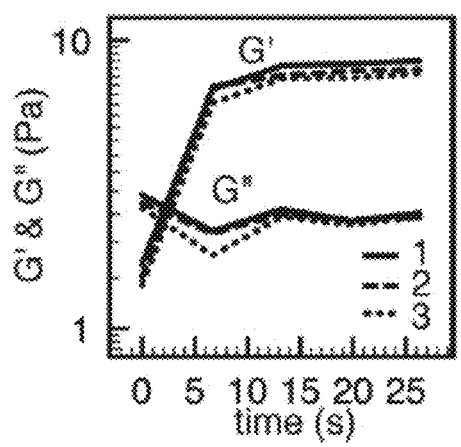
Figure 6:
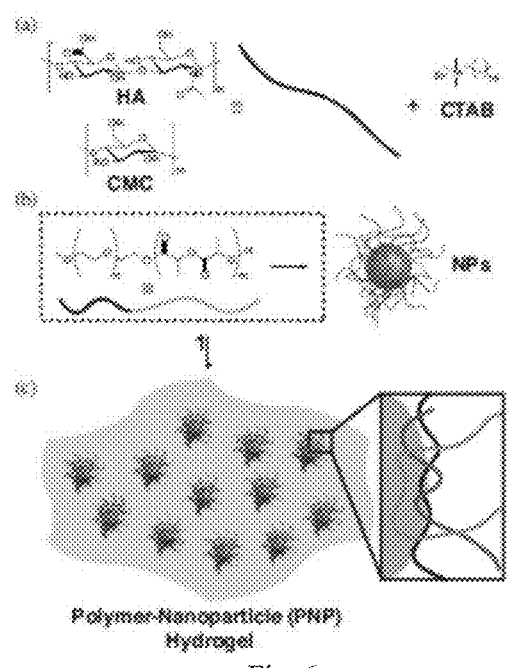
FIG. 6 is a schematic representation of the preparation of polymer nanoparticle (PNP) hydrogels using electrostatic interactions. (a) Negatively charged polymers, i.e. hyaluronic acid (HA) or carboxymethylcellulose (CMC; R=—$CH_2$—COOH), can be non-covalently modified via addition of cetyltrimethylammonium bromide (CTAB). (b) Amphiphilic poly(ethylene glycol)-b-poly(lactic acid) (PEG-b-PLA) polymers can be nanoprecipitated from water to form biodegradable nanoparticles (NPs). (c) PNP hydrogels are prepared by simply mixing PEG-b-PLA NPs with HA/CTAB or CMC/CTAB.

PEG5k-b-PLA$_{20k}$ block copolymers were prepared via organocatalytic ring opening polymerization utilizing 1,8-diazabicyloundec-7-ene (DBU) as a catalyst (FIG. 1c). Core-shell NPs ($D_H$ of about 100 nm according to dynamic light scattering (DLS)) were prepared by nanoprecipitation of the amphiphilic diblock copolymer from dimethyl sulfoxide (DMSO; a good solvent for both blocks) into water (a selective solvent for the hydrophilic PEG block). As with PSNPs, mixing aqueous solutions of HPMC-C$_{12}$ and PEG-b-PLA NPs produced a PNP hydrogel (HPMC-C$_{12}$ 1 wt %: PEG-b-PLA NPs 10 wt %) with analogous mechanical properties (FIGS. 2i, and 2j). The presence of the PEG corona on the NPs dramatically reduced the inherent affinity between the HPMC and the NPs, resulting in a 30-fold increase in shear storage modulus with conjugation of C$_{12}$ moieties relative to nonfunctionalized HPMC (FIG. 2i). Thus, strong adhesion between HPMC-x polymers and PEG-b-PLA NPs, and consequent hydrogel formation, requires the presence of a sufficiently long hydrophobic tail. Moreover, decreasing the size of the PEG corona on the NPs by employing block copolymers with a shorter PEG chain (PEG2k-b-PLA$_{16k}$) led to enhanced PNP interactions and stronger materials (Supplementary FIG. 6). Furthermore, the dynamic nature of the non-covalent interactions was retained in these materials, affording similar stress-induced flow properties and material recovery as for hydrogels formulated with PSNPs (FIG. 2k, 2l). Steady shear measurements on these materials indicated a large change in the viscosity (i.e., a decrease in viscosity of ~$10^3$ Pa s) with an increase of shear rate from a low shear rate (i.e., ~0.1 s$^{-1}$) to a high shear rate (i.e., ~100 s$^{-1}$) shear rates, a beneficial property for facile injection through high gauge needles.

5. Example 6. PNP Hydrogels Containing a Cationic Surfactant

Hydrogels were prepared by first dissolving the polymer of interest (30 mg) in water (1.0 mL) with stirring and mild heating. PEG-b-PLA nanoparticles (Rd 75 nm), were prepared (Cheng, J.; et al., Biomaterials 2007, 28, 869-876) and were concentrated to 15 wt % solutions in water and CTAB was added to the appropriate concentration. To prepare polymer-nanoparticle hydrogels (PNP gels), polymer solutions were combined with NP/CTAB solutions to a finally weight fraction of 1 wt % polymer: 10 wt % NPs: 0.25-0.5% CTAB. PNP gels were mixed well by vortex, mild centrifugation, and agitation to enable homogenization and removal of bubbles. For rheometry measurements, 500 mL of gel was prepared.

6. Example 7. PNP In Vitro Release Studies

Hydrogels prepared as described above except with FITC-labeled BSA (bovine serum albumin) dissolved alongside the HPMC polymer, resulting in a final concentration of BSA of 1 wt % in the hydrogel.

OR (oil-red dye)-loaded PEG-β-PLA NPs were prepared by co-nanoprecipitation of OR with PEG-β-PLA block copolymer. These NPs were then used to prepare hydrogels by the same method described above. Each hydrogel (200 µL) was placed into a 1.5 mL centrifuge tube and deionized water (1.3 mL) was added on top of the hydrogel. The tube was placed into an incubator at 37° C. After certain time periods, 1 mL of the aqueous supernatant solution removed by pipette and the extracted solution was replaced with fresh deionized water. The collected samples were analyzed for solute concentration based on calibration curves prepared using either OR or FITC-Albumin absorbance. All experiments were performed in triplicate.

The BSA was completely retained within the hydrogels upon formation and the release of the BSA into water (an infinite sink) was monitored using UV-vis spectroscopy. The release profile (FIG. 4a) appeared to be governed by Fickian diffusion. Modeling of the release data according to the Ritger-Peppas equation confirmed purely diffusional albumin release (k=18.7%/h; FIG. 4b).

Oil Red, which was encapsulated into the PEG-βNPs during the nanoprecipitation process prior to hydrogel formation, were released from the hydrogels with an entirely different profile (FIG. 4c). This model drug demonstrated a small burst release (<10%), followed by zero-order release (k=0.6%/h), attributable to erosion-based release.

7. Example 8. PNP In Vivo Biocompatibility Studies

All animal procedures were performed according to MIT Animal Care and Use Committee approved protocols. For biocompatibility studies, adult male C57BL/6 mice (8 weeks old) were injected subcutaneously on the back with PNP gels (200 µL; HPMC-C$_{12}$: PEG-β-PLA NPs 1:10 wt %) and PBS (control) using a 26 G syringe. At 3 and 7 days following administration, mice were euthanized and the hydrogel and surrounding tissue was harvested (3 mice per time point). Tissue was fixed for 24 hours in formalin and cross-sections of the skin and underlying material (~40 µm in thickness), embedded in paraffin, were stained with standard haematoxylin and eosin (H&E) or Mason's trichrome.

Histological analysis (FIGS. 5a and b, respectively) demonstrated mild infiltration of the material by neutrophils at day 3, which were replaced primarily by macrophages at day 7. The material was beginning to be cleared by macrophages at this time, with no evidence of multi-nucleated giant cells or lymphocytes, no indication of fibrosis, and no signs of inflammation or damage in the adjacent tissue.

8. Example 9. PNP In Vivo Release Studies

All animal procedures were performed according to MIT Animal Care and Use Committee approved protocols. PNP gels were prepared with BSA-AF (1 wt %; Life Technologies) loaded into the aqueous phase and Texas Red R-DHPE encapsulated within the PEG-β-PLA NPs ([TR]=1 µM in the final gel). Control hydrogels, containing only one of the fluorescent compounds, were similarly prepared. Adult male SKH1E mice (8 weeks old) were injected subcutaneously on the back with PNP gels (200 µL; HPMC-C$_{12}$: PEG-β-PLA NPs 1:10 wt %) using a 26 G syringe.

For in vivo imaging, 8-week old male hairless SKH1-E mice were first maintained on an alfalfa-free diet for two weeks prior to administration to limit background fluorescence. Mice were anesthetized using inhaled isoflurane, and 200 µL was injected subcutaneously into the rear right flank of the animal using a 26 G syringe. Treatment groups consisted of the hydrogel with the combined fluorophores (n=5), the control hydrogel with Texas Red only (n=2), the control hydrogel with BSA-AF (n=2), and a bolus injection of BSA-AF (n=1).

Imaging was conducted on an IVIS® Spectrum in vivo imaging system with a heated stage and an inhaled isoflurane manifold. Fluorescent images were collected at several time-points over the following week, using filter sets of
570/620 (Texas Red) and 675/720 (AF-680) with a 1.5 cm subject height using
small binning and an F-stop of 1.

PNP gels were formulated with a model hydrophobic therapeutic (Texas Red R-DHPE; TR) loaded into PEG-β-PLA NPs and a model hydrophilic
protein therapeutic, Alexa Fluor R 680-conjugated BSA (BSAAF), loaded into the aqueous bulk of the gel. These gels were injected subcutaneously into adult SKH1E (hairless) mice and the release was monitored via intravital fluorescence imaging (FIG. 5c). It was not possible to quantitatively investigate the release rate of the model therapeutics from the hydrogel in vivo on account of photobleaching of the TR dye and changing PNP hydrogel size on account of its moldability. However, a consistent release pattern was observed in the SKH1E mice (n=5) wherein the BSA accessed more of the animal than the TR (FIGS. 5d-f). Furthermore, control experiments with a bolus injection of BSA-FITC highlight that the PNP hydrogels provide sustained release of the BSA in vivo.

Unless defined otherwise, all technical and scientific terms used herein have the same meanings as commonly understood by one of skill in the art to which the disclosed invention belongs. Publications cited herein and the materials for which they are cited are specifically incorporated by reference.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

We claim:

1. A shear-thinning injectable hydrogel comprising:
   one or more biocompatible gel-forming polymers selected from the group consisting of polysaccharides and proteins, optionally modified with one or more ester, carbonate, amide, carbamate, urea, ether or amine-linked capping groups, and
   nanoparticles having a diameter between 10 nm and 1000 nm formed of one or more biocompatible amphiphilic polymers comprising one or more hydrophobic polymers selected from the group consisting of polyanhydrides, poly(ortho)esters, polyesters, polyurethanes, and copolymers comprising the monomers of these polymers and one or more hydrophilic polymers selected from the group consisting of polysaccharides, proteins polyamino acids, polyalkylene oxides,
   optionally including an electrostatic charge enhancing agent,
   wherein the nanoparticles are non-covalently bound to multiple biocompatible gel-forming polymers to form the shear-thinning injectable hydrogel comprising between about 1 and 15 wt % nanoparticles in the shear-thinning injectable hydrogel,
   the hydrogel optionally comprising one or more therapeutic, prophylactic or diagnostic agents encapsulated within the nanoparticles, associated with the surface of the particles and/or dispersed through the hydrogel,
   wherein the dynamic shear viscosity of the shear-thinning injectable hydrogel at a shear rate within the range between $0.1$ $s^{-1}$ and $100$ $s^{-1}$, inclusive, is greater than the sum of the dynamic shear viscosity of a suspension of the nanoparticles and a solution of the one or more biocompatible gel-forming polymers at the shear rate within the range between $0.1$ $s^{-1}$ and $100$ $s^{-1}$, inclusive.

2. The shear-thinning injectable hydrogel of claim 1, wherein the dynamic shear viscosity of the shear-thinning injectable hydrogel at a shear rate within the range between $0.1$ $s^{-1}$ and $100$ $s^{-1}$ is a multiplicative factor of between 2 and 100,000 times, inclusive, greater than the sum of the dynamic shear viscosity of the suspension of nanoparticles and the solution of the one or more biocompatible gel-forming polymers at the shear rate within the range between $0.1$ $s^{-1}$ and $100$ $s^{-1}$, inclusive.

3. The shear-thinning injectable hydrogel of claim 2, wherein the dynamic shear viscosity of the hydrogel at a shear rate within the range between $0.1$ $s^{-1}$ and $100$ $s^{-1}$ is a multiplicative factor of between 2 and 1,000 times, inclusive, greater than the sum of the dynamic shear viscosity of the suspension of nanoparticles and the solution of the one or more biocompatible gel-forming polymers at the shear rate within the range between $0.1$ $s^{-1}$ and $100$ $s^{-1}$, inclusive.

4. The shear-thinning injectable hydrogel of claim 3, wherein the dynamic shear viscosity of the hydrogel at a shear rate within the range between $0.1$ $s^{-1}$ and $100$ $s^{-1}$ is a multiplicative factor of between 10 and 1000 times, inclusive, greater than the sum of the dynamic shear viscosity of the suspension of nanoparticles and the solution of the one or more biocompatible gel-forming polymers at the shear rate within the range between $0.1$ $s^{-1}$ and $100$ $s^{-1}$, inclusive.

5. The shear-thinning injectable hydrogel of claim 4, wherein the dynamic shear viscosity of the shear-thinning injectable hydrogel at a shear rate within the range between $0.1$ $s^{-1}$ and $100$ $s^{-1}$ is a multiplicative factor of between 100 and 1000 times, inclusive, greater than the sum of the dynamic shear viscosity of the suspension of nanoparticles and the solution of the one or more biocompatible gel-forming polymers at the shear rate within the range between $0.1$ $s^{-1}$ and $100$ $s^{-1}$, inclusive.

6. The shear-thinning injectable hydrogel of claim 1, wherein at least one of the one or more biocompatible gel-forming polymers is a polysaccharide selected from the group consisting of celluloses, hyaluronic acids, dextrans, xanthans and combinations thereof.

7. The shear-thinning injectable hydrogel of claim 6, wherein the polysaccharide is a cellulose or a modified cellulose.

8. The shear-thinning injectable hydrogel of claim 7, wherein the cellulose is hydroxypropyl methylcellulose or carboxymethyl cellulose.

9. The shear-thinning injectable hydrogel of claim 1, wherein the one or more biocompatible gel-forming polymers are modified with one or more ester, carbonate, amide, carbamate, urea, ether or amine-linked capping groups.

10. The shear-thinning injectable hydrogel of claim 9, wherein the one or more capping groups are selected from the group consisting of $C_1$-$C_{20}$ alkyl groups, $C_3$-$C_{18}$ cycloalkyl groups, and $C_6$-$C_{18}$ aryl, wherein any of the $C_1$-$C_{20}$ alkyl groups, $C_3$-$C_{18}$ cycloalkyl groups, and $C_6$-$C_{18}$ aryl groups may be unsubstituted or substituted one or more times.

11. The shear-thinning injectable hydrogel of claim 1, wherein the one or more biocompatible gel-forming polymers are at a concentration of between about 0.1 wt. % and about 10 wt. % prior to mixing with the nanoparticles.

12. The shear-thinning injectable hydrogel of claim 1, wherein the one or more biocompatible amphiphilic polymers comprise one or more hydrophobic polymers selected from the group consisting of polymers of lactic acid and glycolic acid, poly(butic acid), poly(valeric acid), poly(caprolactone), poly(hydroxybutyrate), poly(ethylene-co-maleic anhydride), poly(ethylene maleic anhydride-co-L-dopamine), poly(ethylene maleic anhydride-co-phenylalanine), poly(ethylene maleic anhydride-co-tyrosine), poly(butadiene-co-maleic anhydride), poly(butadiene maleic anhydride-co-L-dopamine), poly(butadiene maleic anhydride-co-phenylalanine), poly(butadiene maleic anhydride-co-tyrosine), and copolymers comprising the monomers of these polymers.

13. The shear-thinning injectable hydrogel of claim 1, wherein the nanoparticles comprise a core-shell nanoparticle.

14. The shear-thinning injectable hydrogel of claim 1, wherein the one or more biocompatible amphiphilic polymers are a poly(alkylene oxide)-block-(polyester).

15. The shear-thinning injectable hydrogel of claim 1, wherein the one or more biocompatible amphiphilic polymers are a poly(ethylene glycol)-block-poly(lactic acid).

16. The shear-thinning injectable hydrogel of claim 1, wherein the one or more biocompatible gel-forming polymers are charged at physiological conditions.

17. The shear-thinning injectable hydrogel of claim 1, wherein the one or more biocompatible gel-forming polymers are selected from the group consisting of hyaluronic acid, xanthan, and guar.

18. The shear-thinning injectable hydrogel of claim 17, wherein at least one of the one or more biocompatible gel-forming polymers is hyaluronic acid.

19. The shear-thinning injectable hydrogel of claim 1, wherein the one or more biocompatible gel-forming polymers are selected from the group consisting of aminopolysaccharides and positively charged proteins.

20. The shear-thinning injectable hydrogel of claim 1, further comprising an ionic surfactant.

21. The shear-thinning injectable hydrogel of claim 20, wherein the ionic surfactant is a cationic surfactant when the one or more biocompatible gel-forming polymers are negatively charged at physiological conditions.

22. The shear-thinning injectable hydrogel of claim 21, wherein the cationic surfactant is selected from the group consisting of cetyltrimethylammonium bromide, cetyltrimethylammonium iodide, cetyltrimethylammonium fluoride, and cetyltrimethylammonium chloride.

23. The shear-thinning injectable hydrogel of claim 22, wherein the cationic surfactant is cetyltrimethylammonium bromide.

24. The shear-thinning injectable hydrogel of claim 20, wherein the ionic surfactant is an anionic surfactant when the one or more biocompatible gel-forming polymers are positively charged at physiological conditions.

25. The shear-thinning injectable hydrogel of claim 24, wherein the anionic surfactant is selected from the group consisting of sodium dodecyl sulfate, sodium stearate, and charged fatty acid surfactants.

26. The shear-thinning injectable hydrogel of claim 10, wherein the one or more biocompatible gel-forming polymers comprise hydrophobic capping groups selected from the group consisting of hexyl, dodecyl, and adamantyl.

27. The shear-thinning injectable hydrogel of claim 1, further comprising one or more therapeutic, prophylactic, and/or diagnostic agents.

28. A pharmaceutical composition, comprising the shear-thinning injectable hydrogel of claim 1 comprising one or more therapeutic, prophylactic or diagnostic agents encapsulated within the nanoparticles, associated with the surface of the particles and/or dispersed through the hydrogel and one or more pharmaceutically acceptable carriers.

29. The composition of claim 28, wherein the one or more pharmaceutically acceptable carriers are suitable for parenteral administration.

30. The shear-thinning injectable hydrogel of claim 1, wherein the nanoparticles have a hydrodynamic diameter ($D_H$) between about 10 nm and about 250 nm, as measured by dynamic light scattering.

31. The shear-thinning injectable hydrogel of claim 1, wherein the persistence length of the one or more biocompatible gel-forming polymers is greater than or equal to the hydrodynamic diameter of at least one of the nanoparticles ($lp \geq D_H$).

32. The shear-thinning injectable hydrogel of claim 1, having a viscosity less than 1 Pa s at a shear-rate of ~100 $s^{-1}$.

33. The shear-thinning injectable hydrogel claim 1, having a shear storage modulus of G' of between about 5 Pa and about 100,000 Pa at a frequency of 10 rad/s, as measured by oscillatory shear rheometry in the linear viscoelastic regime.

34. A method for making a polymeric gel for administering a therapeutic, prophylactic or diagnostic agent to a subject in need thereof comprising:
  providing one or more biocompatible gel-forming polymers selected from the group consisting of polysaccharides and proteins, optionally modified with one or more ester, carbonate, amide, carbamate, urea, ether or amine-linked capping groups, and
  nanoparticles having a diameter between 10 nm and 1000 nm formed of one or more biocompatible amphiphilic polymers comprising one or more hydrophobic polymers selected from the group consisting of polyanhydrides, poly(ortho)esters, polyesters, polyurethanes, and copolymers comprising the monomers of these polymers and one or more hydrophilic polymers selected from the group consisting of polysaccharides, proteins polyamino acids, polyalkylene oxides,
  optionally including an electrostatic charge enhancing agent,
  wherein the nanoparticles are non-covalently bound to multiple biocompatible gel-forming polymers to form a shear-thinning injectable hydrogel comprising between about 1 and 15 wt % nanoparticles in the shear-thinning injectable hydrogel, and
  wherein the dynamic shear viscosity of the shear-thinning injectable hydrogel at a shear rate within the range between 0.1 $s^{-1}$ and 100 $s^{-1}$, inclusive, is greater than the sum of the dynamic shear viscosity of a suspension of the nanoparticles and a solution of the one or more biocompatible gel-forming polymers at the shear rate within the range between 0.1 $s^{-1}$ and 100 $s^{-1}$, inclusive, and
  encapsulating within the nanoparticles, associating with the surface of the particles and/or dispersing through the hydrogel one or more therapeutic, prophylactic or diagnostic agents.

35. The method of claim 34, wherein the gel is formulated for administration by injection.

36. The shear-thinning injectable hydrogel of claim 19, wherein the one or more biocompatible gel-forming is polymers are a chitosan.

\* \* \* \* \*

UNITED STATES PATENT AND TRADEMARK OFFICE
CERTIFICATE OF CORRECTION

| | |
|---|---|
| PATENT NO. | : 11,045,429 B2 |
| APPLICATION NO. | : 15/412935 |
| DATED | : June 29, 2021 |
| INVENTOR(S) | : Eric A. Appel, Mark W. Tibbitt and Robert S. Langer |

Page 1 of 1

It is certified that error appears in the above-identified patent and that said Letters Patent is hereby corrected as shown below:

In the Specification

Column 1, Lines 19-21, replace "This invention was made with government support under Grant RO 1 DE0156516 to Robert S. Langer, awarded by the National Institutes of Health" with --This invention was made with Government support under Grant No (s) R01 DE016516 awarded by The National Institute of Health (NIH)--.

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*